United States Patent
Koo

(10) Patent No.: US 7,659,977 B2
(45) Date of Patent: Feb. 9, 2010

(54) APPARATUS AND METHOD FOR IMAGING WITH SURFACE ENHANCED COHERENT ANTI-STOKES RAMAN SCATTERING (SECARS)

(75) Inventor: Tae-Woong Koo, Cupertino, CA (US)

(73) Assignee: Intel Corporation, Santa Clara, CA (US)

( * ) Notice: Subject to any disclaimer, the term of this patent is extended or adjusted under 35 U.S.C. 154(b) by 239 days.

(21) Appl. No.: 11/408,185

(22) Filed: Apr. 21, 2006

(65) Prior Publication Data
US 2007/0247620 A1  Oct. 25, 2007

(51) Int. Cl.
G01J 3/44 (2006.01)
(52) U.S. Cl. ...................................... 356/301
(58) Field of Classification Search .................. 356/301
See application file for complete search history.

(56) References Cited

U.S. PATENT DOCUMENTS

| | | | |
|---|---|---|---|
| 658,397 A | | 9/1900 | Oscar |
| 5,609,907 A | * | 3/1997 | Natan .......................... 427/2.12 |
| 5,818,047 A | | 10/1998 | Chaney et al. |
| 6,002,471 A | | 12/1999 | Quake |
| 6,108,081 A | * | 8/2000 | Holtom et al. ............... 356/301 |
| 6,174,677 B1 | | 1/2001 | Vo-Dinh |
| 6,583,397 B2 | * | 6/2003 | Vo-Dinh ................... 250/201.5 |
| 6,743,581 B1 | | 6/2004 | Vo-Dinh |
| 6,747,735 B2 | | 6/2004 | Chen et al. |
| 6,798,507 B2 | * | 9/2004 | Xie et al. ..................... 356/301 |
| 6,934,020 B2 | * | 8/2005 | Shimada ..................... 356/301 |
| 7,092,086 B2 | * | 8/2006 | Knebel ....................... 356/301 |
| 7,248,360 B2 | * | 7/2007 | Horchner et al. ............ 356/318 |
| 2005/0084980 A1 | | 4/2005 | Koo et al. |
| 2005/0110990 A1 | | 5/2005 | Koo et al. |

OTHER PUBLICATIONS

Koo et al , Single-molecule detection of biomolecules by surface-enhanced coherent anti-Stokes Raman scattering, May 1, 2005, Optical Society of America, vol. 30, No. 9.*

E.J. Liang et al, Experimental observation of surface enhanced coherent anti-Stokes Raman scattering, Chemical Physics Letters, Sep. 1994.*

* cited by examiner

*Primary Examiner*—L. G Lauchman
(74) *Attorney, Agent, or Firm*—Pillsbury Winthrop Shaw Pittman LLP

(57) ABSTRACT

The embodiments of the invention are directed to improved SERS and SECARS devices and method of manufacturing and using the same. In one embodiment of the invention, a device having at least one laser, a sample stage and a detector, wherein the sample stage is moveable and has as SERS active material is disclosed. In another embodiment of the invention, the device has at least one laser, a scanning mirror, a sample stage having a SERS active material and a detector, wherein the scanning mirror is adapted to steer a laser beam across a surface of the sample stage.

37 Claims, 14 Drawing Sheets

LF, laser line filter; HW, half-waveplate; DM, dichroic mirror; BF, bandpass filter; P, polarizer; MO, microscope objective; S, sample; ST, sample stage; CCD, charge coupled device camera LF, laser line filter; HW, half-waveplate; DM, dichroic mirror; BF, bandpass filter; P, polarizer; MO, microscope objective; S, sample, ST, sample stage; CCD, charge coupled device camera LF, laser line filter; HW, half-waveplate; DM, dichroic mirror; BF, bandpass filter; P, polarizer; MO, microscope objective; S, sample; CCD, charge coupled device camera OPO, optical parametric oscillator; LF, laser line filter; HW, half-waveplate; DM, dichroic mirror; BF, bandpass filter; P, polarizer; MO, microscope objective; S, sample; CCD, charge coupled device camera OPO, optical parametric oscillator; LF, laser line filter; HW, half-waveplate; DM, dichroic mirror; BF, bandpass filter; P, polarizer; MO, microscope objective; S, sample; CCD, charge coupled device camera LF, laser line filter; HW, half-waveplate; DM, dichroic mirror; BF, bandpass filter; P, polarizer; SM, scanning mirror; MO, microscope objective; S, sample; CCD, charge coupled device camera LF, laser line filter; HW, half-waveplate; DM, dichroic mirror; BF, bandpass filter; P, polarizer; MO, microscope objective; S, sample; PD, photodiode LF, laser line filter; HW, half-waveplate; DM, dichroic mirror; BF, bandpass filter; P, polarizer; MO, microscope objective; S, sample; PD, photodiode LF, laser line filter; DM, dichroic mirror; BF, bandpass filter; MO, microscope objective; S, sample.

A

B

APPARATUS AND METHOD FOR IMAGING WITH SURFACE ENHANCED COHERENT ANTI-STOKES RAMAN SCATTERING (SECARS)

RELATED APPLICATIONS

This application is related to U.S. application Ser. Nos.: (1) 10/688,680, filed Oct. 17, 2003, published as US 2005/0084980 A1 on Apr. 21, 2005, (2) 10/966,893, filed Oct. 15, 2004, published as US 2005/0110990 A1 on May 26, 2005, (3) U.S. Ser. No. 11/239,100, filed Sep. 30, 2005, (4) U.S. Ser. No. 11/305,335, filed Dec. 19, 2005, and (5) U.S. Ser. No. 11/394,157, filed Mar. 31, 2006, which are incorporated herein by reference.

FIELD OF INVENTION

Embodiments of the invention relate to the field of molecular analysis by spectroscopy. The invention relates generally to methods and devices for use in biological, biochemical, and chemical testing, and particularly to methods, instruments, and the use of instruments which utilize surface enhanced coherent anti-Stokes Raman spectroscopy (SECARS) for detecting, identifying, or sequencing molecules, such as nucleic acids. More specifically, the embodiments of the invention relate to (a) an improved SECARS instrument which beam steering or sample positioning capabilities; (b) method of imaging a sample with the improved SECARS instrument; and (c) method of manufacturing the improved SECARS instrument.

BACKGROUND

Raman spectroscopy is a spectroscopic technique used in condensed matter physics, chemistry, biology and medical diagnostics, among others, to study vibrational, rotational, and other low-frequency modes in a system. It relies on inelastic scattering, or Raman scattering of monochromatic light, usually from a laser in the visible, near infrared, or near ultraviolet range. Typically, photons are absorbed or emitted by the laser light, resulting in the energy of the laser photons being shifted up or down. The shift in energy gives information about the phonon modes in the system. Infrared spectroscopy yields similar, but complementary information.

Typically, a sample is illuminated with a laser beam. Light from the illuminated spot is collected with a lens and sent through a monochromator. Wavelengths close to the laser line (due to elastic Rayleigh scattering) are filtered out and those in a certain spectral window away from the laser line are dispersed onto a detector.

Spontaneous Raman scattering is typically very weak, and as a result the main difficulty of Raman spectroscopy is separating the weak inelastically scattered light from the intense Rayleigh scattered laser light. Raman spectrometers typically use holographic diffraction gratings and multiple dispersion stages to achieve a high degree of laser rejection. A photon-counting photomultiplier tube (PMT) or, more commonly, a CCD camera is used to detect the Raman scattered light.

The Raman effect occurs when light impinges upon a molecule and interacts with the electron cloud of the bonds of that molecule. The amount of deformation of the electron cloud is the polarizability of the molecule. The amount of the polarizability of the bond will determine the intensity and frequency of the Raman shift. The photon (light quantum), excites one of the electrons into a virtual state. When the photon is released the molecule relaxes back into a vibrational energy state as shown in FIG. 1. For example, when the molecule relaxes into the zero vibrational energy state (i.e., "ground state"), it generates Rayleigh scattering. The molecule could relax into the first vibration energy states, and this generates Stokes Raman scattering. However, if the molecule was already in an elevated vibrational energy state such as the first vibrational energy state and it relaxes into the zero vibrational energy state, the Raman scattering is then called Anti-Stokes Raman scattering. By Stokes Raman scattering, the wavelength of the emitted light is longer than the wavelength of the excitatory light. By anti-Stokes Raman scattering, the wavelength of the emitted light is shorter that the wavelength of the excitatory light.

The sensitive and accurate detection, identification and multiplexed molecular imaging of different chemical/biological composition inside a sample with single molecule sensitivity and high multiplicity has not been done. Even the detection and identification of small numbers (<1000) of molecules from biological and other samples has proven to be an elusive goal, despite widespread potential uses in medical diagnostics, pathology, toxicology, environmental sampling, chemical analysis, forensics and numerous other fields. The embodiments of this invention address these problems in the current state of the art.

DETAILED DESCRIPTION

Figure 1:
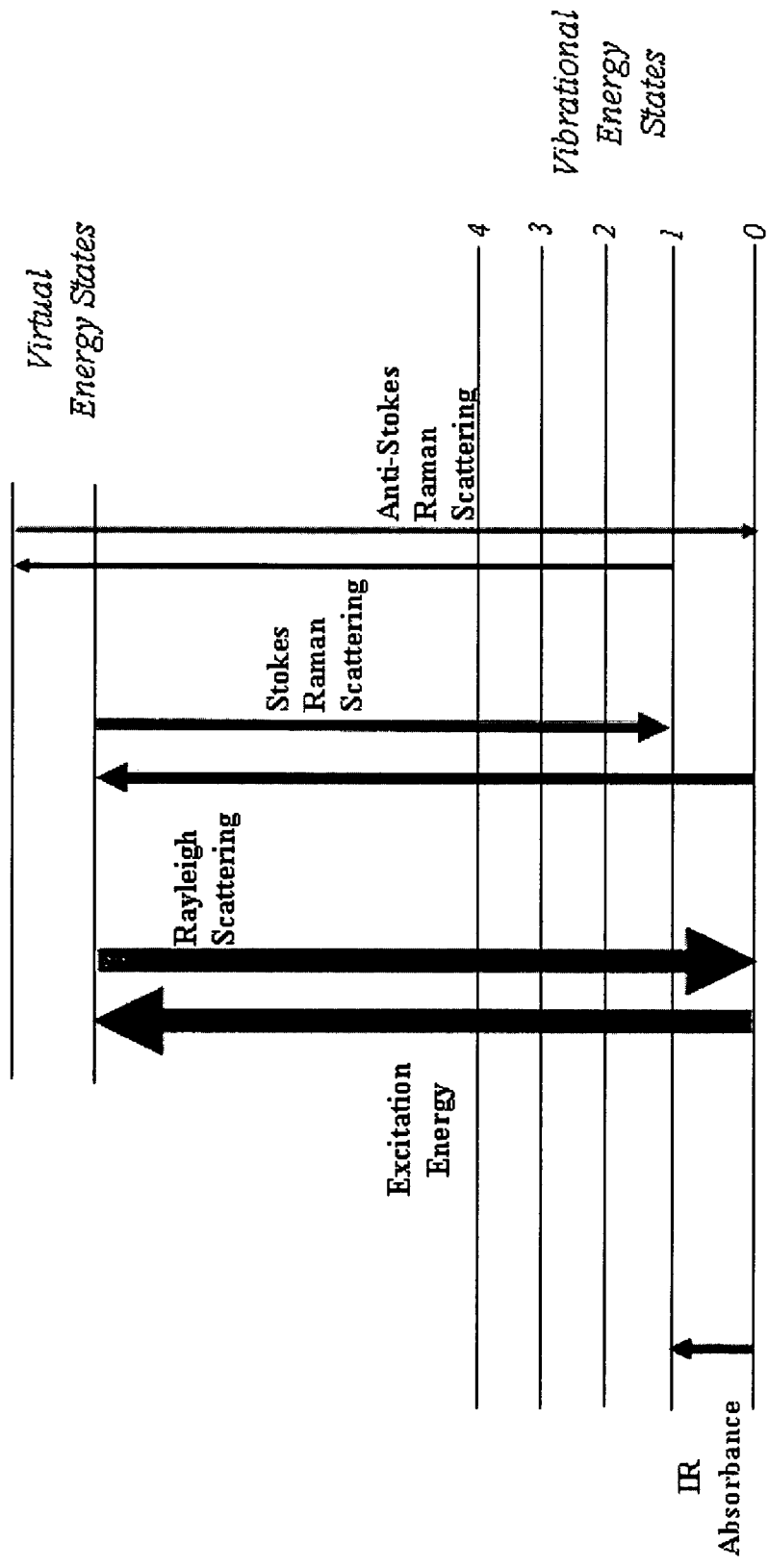
FIG. 1 shows vibrational energy states of molecules undergoing Rayleigh scattering, Stokes Raman scattering and anti-Stokes Raman scattering.

As used in the specification and claims, the singular forms "a", "an" and "the" include plural references unless the context clearly dictates otherwise. For example, the term "an array" may include a plurality of arrays unless the context clearly dictates otherwise.

An "array," "macroarray" or "microarray" is an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, or other solid supports. The array could either be a macroarray or a microarray, depending on the size of the sample spots on the array. A macroarray generally contains sample spot sizes of about 300 microns or larger and can be easily imaged by gel and blot scanners. A microarray would generally contain spot sizes of less than 300 microns.

"Solid support," "support," and "substrate" refer to a material or group of materials having a rigid or semi-rigid surface or surfaces. In some aspects, at least one surface of the solid support will be substantially flat, although in some aspects it may be desirable to physically separate synthesis regions for different molecules with, for example, wells, raised regions, pins, etched trenches, or the like. In certain aspects, the solid support(s) will take the form of beads, resins, gels, microspheres, or other geometric configurations.

The term "target" or "target molecule" refers to a molecule of interest that is to be analyzed, e.g., a nucleotide, an oligonucleotide, or a protein. The target or target molecule could be a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to molecular probes such as chemically modified carbon nanotubes, carbon nanotube bundles, nanowires, nanoclusters or nanoparticles. The target molecule may be fluorescently labeled DNA or RNA.

The term "probe" or "probe molecule" refers to a molecule that binds to a target molecule for the analysis of the target. The probe or probe molecule is generally, but not necessarily, has a known molecular structure or sequence. The probe or probe molecule is generally, but not necessarily, attached to the substrate of the array. The probe or probe molecule is typically a nucleotide, an oligonucleotide, or a protein, including, for example, cDNA or pre-synthesized polynucleotide deposited on the array. Probes molecules are biomolecules capable of undergoing binding or molecular recognition events with target molecules. (In some references, the terms "target" and "probe" are defined opposite to the definitions provided here.) The polynucleotide probes require only the sequence information of genes, and thereby can exploit the genome sequences of an organism. In cDNA arrays, there could be cross-hybridization due to sequence homologies among members of a gene family. Polynucleotide arrays can be specifically designed to differentiate between highly homologous members of a gene family as well as spliced forms of the same gene (exon-specific). Polynucleotide arrays of the embodiment of this invention could also be designed to allow detection of mutations and single nucleotide polymorphism. A probe or probe molecule can be a capture molecule.

The term "capture molecule" refers to a molecule that is immobilized on a surface. The capture molecule is generally, but not necessarily, binds to a target or target molecule. The capture molecule is typically a nucleotide, an oligonucleotide, or a protein, but could also be a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to a target molecule that is bound to a probe molecule to form a complex of the capture molecule, target molecule and the probe molecule. The capture molecule may be fluorescently labeled DNA or RNA. The capture molecule may or may not be capable of binding to just the target molecule or just the probe molecule.

The terms "die," "polymer array chip," "DNA array," "array chip," "DNA array chip," or "bio-chip" are used interchangeably and refer to a collection of a large number of probes arranged on a shared substrate which could be a portion of a silicon wafer, a nylon strip or a glass slide.

The term "chip" or "microchip" refers to a microelectronic device made of semiconductor material and having one or more integrated circuits or one or more devices. A "chip" or "microchip" is typically a section of a wafer and made by slicing the wafer. A "chip" or "microchip" may comprise many miniature transistors and other electronic components on a single thin rectangle of silicon, sapphire, germanium, silicon nitride, silicon germanium, or of any other semiconductor material. A microchip can contain dozens, hundreds, or millions of electronic components.

The term "molecule" generally refers to a macromolecule or polymer as described herein. However, arrays comprising single molecules, as opposed to macromolecules or polymers, are also within the scope of the embodiments of the invention.

"Predefined region" or "spot" or "pad" refers to a localized area on a solid support. The spot could be intended to be used for formation of a selected molecule and is otherwise referred to herein in the alternative as a "selected" region. The spot may have any convenient shape, e.g., circular, rectangular, elliptical, wedge-shaped, etc. For the sake of brevity herein, "predefined regions" are sometimes referred to simply as "regions" or "spots." In some embodiments, a predefined region and, therefore, the area upon which each distinct molecule is synthesized is smaller than about 1 cm$^2$ or less than 1 mm$^2$, and still more preferably less than 0.5 mm$^2$. In most preferred embodiments the regions have an area less than about 10,000 μm$^2$ or, more preferably, less than 100 μm$^2$, and even more preferably less than 10 μm$^2$ or less than 1 μm$^2$. Additionally, multiple copies of the polymer will typically be synthesized within any preselected region. The number of copies can be in the hundreds to the millions. A spot could contain an electrode to generate an electrochemical reagent, a working electrode to synthesize a polymer and a confinement electrode to confine the generated electrochemical reagent. The electrode to generate the electrochemical reagent could be of any shape, including, for example, circular, flat disk shaped and hemisphere shaped.

"Micro-Electro-Mechanical Systems (MEMS)" is the integration of mechanical elements, sensors, actuators, and electronics on a common silicon substrate through microfabrication technology. While the electronics are fabricated using integrated circuit (IC) process sequences (e.g., CMOS, Bipolar, or BICMOS processes), the micromechanical components could be fabricated using compatible "micromachining" processes that selectively etch away parts of the silicon wafer or add new structural layers to form the mechanical and electromechanical devices. Microelectronic integrated circuits can be thought of as the "brains" of a system and MEMS augments this decision-making capability with "eyes" and "arms", to allow microsystems to sense and control the environment. Sensors gather information from the environment through measuring mechanical, thermal, biological, chemical, optical, and magnetic phenomena. The electronics then process the information derived from the sensors and through some decision making capability direct the actuators to respond by moving, positioning, regulating, pumping, and filtering, thereby controlling the environment for some desired outcome or purpose. Because MEMS devices are manufactured using batch fabrication techniques similar to those used for integrated circuits, unprecedented levels of functionality, reliability, and sophistication can be placed on a small silicon chip at a relatively low cost.

"Microprocessor" is a processor on an integrated circuit (IC) chip. The processor may be one or more processor on one or more IC chip. The chip is typically a silicon chip with thousands of electronic components that serves as a central processing unit (CPU) of a computer or a computing device.

A "macromolecule" or "polymer" comprises two or more monomers covalently joined. The monomers may be joined one at a time or in strings of multiple monomers, ordinarily known as "oligomers." Thus, for example, one monomer and a string of five monomers may be joined to form a macromolecule or polymer of six monomers. Similarly, a string of fifty monomers may be joined with a string of hundred monomers to form a macromolecule or polymer of one hundred and fifty monomers. The term polymer as used herein includes, for example, both linear and cyclic polymers of nucleic acids, polynucleotides, polynucleotides, polysaccharides, oligosaccharides, proteins, polypeptides, peptides, phospholipids and peptide nucleic acids (PNAs). The peptides include those peptides having either α-, β-, or ω-amino acids. In addition, polymers include heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be apparent upon review of this disclosure.

A "nanomaterial" as used herein refers to a structure, a device or a system having a dimension at the atomic, molecular or macromolecular levels, in the length scale of approximately 1-100 nanometer range. Preferably, a nanomaterial has properties and functions because of the size and can be manipulated and controlled on the atomic level.

A "carbon nanotube" refers to a fullerene molecule having a cylindrical or toroidal shape. A "fullerene" refers to a form of carbon having a large molecule consisting of an empty cage of sixty or more carbon atoms.

The term "nucleotide" includes deoxynucleotides and analogs thereof. These analogs are those molecules having some structural features in common with a naturally occurring nucleotide such that when incorporated into a pplynucleotide sequence, they allow hybridization with a complementary polynucleotide in solution. Typically, these analogs are derived from naturally occurring nucleotides by replacing and/or modifying the base, the ribose or the phosphodiester moiety. The changes can be tailor-made to stabilize or destabilize hybrid formation, or to enhance the specificity of hybridization with a complementary polynucleotide sequence as desired, or to enhance stability of the polynucleotide.

The term "polynucleotide" or "nucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. Polynucleotides of the embodiments of the invention include sequences of deoxyribopolynucleotide (DNA), ribopolynucleotide (RNA), or DNA copies of ribopolynucleotide (cDNA) which may be isolated from natural sources, recombinantly produced, or artificially synthesized. A further example of a polynucleotide of the embodiments of the invention may be polyamide polynucleotide (PNA). The polynucleotides and nucleic acids may exist as single-stranded or double-stranded. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. The polymers made of nucleotides such as nucleic acids, polynucleotides and polynucleotides may also be referred to herein as "nucleotide polymers."

An "oligonucleotide" is a polynucleotide having 2 to 20 nucleotides. Analogs also include protected and/or modified monomers as are conventionally used in polynucleotide synthesis. As one of skill in the art is well aware, polynucleotide synthesis uses a variety of base-protected nucleoside derivatives in which one or more of the nitrogens of the purine and pyrimidine moiety are protected by groups such as dimethoxytrityl, benzyl, tert-butyl, isobutyl and the like.

For instance, structural groups are optionally added to the ribose or base of a nucleoside for incorporation into a polynucleotide, such as a methyl, propyl or allyl group at the 2'-O position on the ribose, or a fluoro group which substitutes for the 2'-O group, or a bromo group on the ribonucleoside base. 2'-O-methyloligoribonucleotides (2'—O-MeORNs) have a higher affinity for complementary polynucleotides (especially RNA) than their unmodified counterparts. Alternatively, deazapurines and deazapyrimidines in which one or more N atoms of the purine or pyrimidine heterocyclic ring are replaced by C atoms can also be used.

The phosphodiester linkage, or "sugar-phosphate backbone" of the polynucleotide can also be substituted or modified, for instance with methyl phosphonates, O-methyl phosphates or phosphororthioates. Another example of a polynucleotide comprising such modified linkages for purposes of this disclosure includes "peptide polynucleotides" in which a polyamide backbone is attached to polynucleotide bases, or modified polynucleotide bases. Peptide polynucleotides which comprise a polyamide backbone and the bases found in naturally occurring nucleotides are commercially available.

Nucleotides with modified bases can also be used in the embodiments of the invention. Some examples of base modifications include 2-aminoadenine, 5-methylcytosine, 5-(propyn-1-yl)cytosine, 5-(propyn-1-yl)uracil, 5-bromouracil, 5-bromocytosine, hydroxymethylcytosine, methyluracil, hydroxymethyluracil, and dihydroxypentyluracil which can be incorporated into polynucleotides in order to modify binding affinity for complementary polynucleotides.

Groups can also be linked to various positions on the nucleoside sugar ring or on the purine or pyrimidine rings which may stabilize the duplex by electrostatic interactions with the negatively charged phosphate backbone, or through interactions in the major and minor groves. For example, adenosine and guanosine nucleotides can be substituted at the $N^2$ position with an imidazolyl propyl group, increasing duplex stability. Universal base analogues such as 3-nitropyrrole and 5-nitroindole can also be included. A variety of modified polynucleotides suitable for use in the embodiments of the invention are described in the literature.

When the macromolecule of interest is a peptide, the amino acids can be any amino acids, including α, β, or ω-amino acids. When the amino acids are α-amino acids, either the L-optical isomer or the D-optical isomer may be used. Additionally, unnatural amino acids, for example, β-alanine, phenylglycine and homoarginine are also contemplated by the embodiments of the invention. These amino acids are well-known in the art.

A "peptide" is a polymer in which the monomers are amino acids and which are joined together through amide bonds and alternatively referred to as a polypeptide. In the context of this specification it should be appreciated that the amino acids may be the L-optical isomer or the D-optical isomer. Peptides are two or more amino acid monomers long, and often more than 20 amino acid monomers long.

A "protein" is a long polymer of amino acids linked via peptide bonds and which may be composed of two or more polypeptide chains. More specifically, the term "protein" refers to a molecule composed of one or more chains of amino acids in a specific order; for example, the order as determined by the base sequence of nucleotides in the gene coding for the protein. Proteins are essential for the structure, function, and regulation of the body's cells, tissues, and organs, and each protein has unique functions. Examples are hormones, enzymes, and antibodies.

The term "sequence" refers to the particular ordering of monomers within a macromolecule and it may be referred to herein as the sequence of the macromolecule.

The term "hybridization" refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." For example, hybridization refers to the formation of hybrids between a probe polynucleotide (e.g., a polynucleotide of the invention which may include substitutions, deletion, and/or additions) and a specific target polynucleotide (e.g., an analyte polynucleotide) wherein the probe preferentially hybridizes to the specific target polynucleotide and substantially does not hybridize to polynucleotides consisting of sequences which are not substantially complementary to the target polynucleotide. However, it will be recognized by those of skill that the minimum length of a polynucleotide desired for specific hybridization to a target polynucleotide will depend on several factors: G/C content, positioning of mismatched bases (if any), degree of uniqueness of the sequence as compared to the population of target polynucleotides, and chemical nature of the polynucleotide (e.g., methylphosphonate backbone, phosphorothiolate, etc.), among others.

Methods for conducting polynucleotide hybridization assays have been well developed in the art. Hybridization assay procedures and conditions will vary depending on the application and are selected in accordance with the general binding methods known in the art.

It is appreciated that the ability of two single stranded polynucleotides to hybridize will depend upon factors such as their degree of complementarity as well as the stringency of the hybridization reaction conditions.

As used herein, "stringency" refers to the conditions of a hybridization reaction that influence the degree to which polynucleotides hybridize. Stringent conditions can be selected that allow polynucleotide duplexes to be distinguished based on their degree of mismatch. High stringency is correlated with a lower probability for the formation of a duplex containing mismatched bases. Thus, the higher the stringency, the greater the probability that two single-stranded polynucleotides, capable of forming a mismatched duplex, will remain single-stranded. Conversely, at lower stringency, the probability of formation of a mismatched duplex is increased.

The appropriate stringency that will allow selection of a perfectly-matched duplex, compared to a duplex containing one or more mismatches (or that will allow selection of a particular mismatched duplex compared to a duplex with a higher degree of mismatch) is generally determined empirically. Means for adjusting the stringency of a hybridization reaction are well-known to those of skill in the art.

A "ligand" is a molecule that is recognized by a particular receptor. Examples of ligands that can be investigated by this invention include, but are not restricted to, agonists and antagonists for cell membrane receptors, toxins and venoms, viral epitopes, hormones, hormone receptors, peptides, enzymes, enzyme substrates, cofactors, drugs (e.g. opiates, steroids, etc.), lectins, sugars, polynucleotides, nucleic acids, oligosaccharides, proteins, and monoclonal antibodies.

A "receptor" is molecule that has an affinity for a given ligand. Receptors may-be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term "receptors" is used herein, no difference in meaning is intended. A "Ligand Receptor Pair" is formed when two macromolecules have combined through molecular recognition to form a complex. Other examples of receptors which can be investigated by this invention include but are not restricted to:

a) Microorganism receptors: Determination of ligands which bind to receptors, such as specific transport proteins or enzymes essential to survival of microorganisms, is useful in developing a new class of antibiotics. Of particular value would be antibiotics against opportunistic fungi, protozoa, and those bacteria resistant to the antibiotics in current use.

b) Enzymes: For instance, one type of receptor is the binding site of enzymes such as the enzymes responsible for cleaving neurotransmitters; determination of ligands which bind to certain receptors to modulate the action of the enzymes which cleave the different neurotransmitters is useful in the development of drugs which can be used in the treatment of disorders of neurotransmission.

c) Antibodies: For instance, the invention may be useful in investigating the ligand-binding site on the antibody molecule which combines with the epitope of an antigen of interest; determining a sequence that mimics an antigenic epitope may lead to the-development of vaccines of which the immunogen is based on one or more of such sequences or lead to the development of related diagnostic agents or compounds useful in therapeutic treatments such as for auto-immune diseases (e.g., by blocking the binding of the "anti-self" antibodies).

d) Nucleic Acids: Sequences of nucleic acids may be synthesized to establish DNA or RNA binding sequences.

e) Catalytic Polypeptides: Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant.

f) Hormone receptors: Examples of hormones receptors include, e.g., the receptors for insulin and growth hormone. Determination of the ligands which bind with high affinity to a receptor is useful in the development of, for example, an oral replacement of the daily injections which diabetics take to relieve the symptoms of diabetes. Other examples are the vasoconstrictive hormone receptors; determination of those ligands which bind to a receptor may lead to the development of drugs to control blood pressure.

g) Opiate receptors: Determination of ligands which bind to the opiate receptors in the brain is useful in the development of less-addictive replacements for morphine and related drugs.

The phrase "SERS active material" or "SERS active particle" refers to a material or a particle that produces a surface-enhanced Raman scattering effect. The SERS active material or particle generates surface enhanced Raman signal specific to the analyte molecules when the analyte-particle complexes are excited with a light source as compared to the Raman signal from the analyte alone in the absence of the SERS active material or SERS active particle. The enhanced Raman scattering effect provides a greatly enhanced Raman signal from Raman-active analyte molecules that have been adsorbed onto certain specially-prepared SERS active surfaces. The SERS active surface could be planar or curved. Typically, the SERS active surfaces are metal surfaces. Increases in the intensity of Raman signal could be in the order of $10^4$-$10^{14}$ for some systems. SERS active material or particle includes a variety of metals including coinage (Au, Ag, Cu), alkalis (Li, Na, K), Al, Pd and Pt. In the case of SERS active particle, the particle size of SERS active particles could range from 1 to 5000 nanometers, preferably in the range of 5 to 250 nanometers, more preferably in the range of 10 to 150 nanometers, and most preferably 40 to 80 nanometers. In one embodiment, there are provided methods for producing metallic colloids to produce SER active material or particles. Such methods can be performed, for example, by mixing metal cations with a reducing agent in aqueous solution, and heating the aqueous solution to about 95° C., thereby producing metallic colloids.

As used herein, the term "colloid" refers to nanometer size metal particles suspending in a liquid, usually an aqueous solution. In the methods of the invention, the metal cations and reducing agent are mixed in aqueous solution prior to heating. This method results in a 50% enhancement of SERS signals obtained from such colloids, and also results in an increase in reproducibility from 10-20% to 80-100%. Typical metals contemplated for use in the practice of the invention include, for example, silver, gold, platinum, copper, aluminum, and the like. A variety of reducing agents are contemplated for use in the practice of the invention, such as for example, citrate, borohydride, and the like. Sodium citrate is used in certain embodiments of the invention. Typically, the metal cations and reducing agent are each present in aqueous solution at a concentration of at least about 0.5 mM. After mixing the metal cations and reducing agent, the solution is heated for about 30 minutes. In some embodiments, the solution is heated for about 60 minutes. Typically, the solution is heated to about 95° C. In other embodiments, the solution is heated to about 100° C. Heating of the solution is accomplished in a variety of ways well known to those skilled in the art. In some embodiments, the heating is accomplished using a microwave oven, a convection oven, or a combination thereof. The methods for producing metallic colloids described herein are in contrast to prior methods wherein a boiling silver nitrate solution is titrated with a sodium citrate solution. This titration method can produce one batch of silver particles with adequate Raman enhancement to dAMP in about 10 attempts, and the other batches have low or no Raman activity at all. However, by employing the methods of the invention, an average SERS signal enhancement of 150% is observed relative to colloids prepared from the titration method.

The term "COIN" refers to a composite-organic-inorganic nanoparticle(s). The COIN could be surface-enhanced Raman scattering (SERS, also referred to as surface-enhanced Raman spectroscopy)-active nanoclusters incorporated into a gel matrix and used in certain other analyte separation techniques described herein. COINs are composite organic-inorganic nanoclusters. These SERS-active probe constructs comprise a core and a surface, wherein the core comprises a metallic colloid comprising a first metal and a Raman-active organic compound. The COINs can further comprise a second metal different from the first metal, wherein the second metal forms a layer overlying the surface of the nanoparticle. The COINs can further comprise an organic layer overlying the metal layer, which organic layer comprises the probe. Suitable probes for attachment to the surface of the SERS-active nanoclusters include, without limitation, antibodies, antigens, polynucleotides, oligonucleotides, receptors, ligands, and the like.

The metal required for achieving a suitable SERS signal is inherent in the COIN, and a wide variety of Raman-active organic compounds can be incorporated into the particle. Indeed, a large number of unique Raman signatures can be created by employing nanoclusters containing Raman-active organic compounds of different structures, mixtures, and ratios. Thus, the methods described herein employing COINs are useful for the simultaneous detection of many multiple components such as analytes in a sample, resulting in rapid qualitative analysis of the contents of "profile" of a body fluid. In addition, since many COINs can be incorporated into a single nanoparticle, the SERS signal from a single COIN particle is strong relative to SERS signals obtained from Raman-active materials that do not contain the nanoclusters described herein as COINs. This situation results in increased sensitivity compared to Raman-techniques that do not utilize COINs.

COINs could be prepared using standard metal colloid chemistry. The preparation of COINs also takes advantage of the ability of metals to adsorb organic compounds. Indeed, since Raman-active organic compounds are adsorbed onto the metal during formation of the metallic colloids, many Raman-active organic compounds can be incorporated into the COIN without requiring special attachment chemistry.

In general, the COINs could be prepared as follows. An aqueous solution is prepared containing suitable metal cations, a reducing agent, and at least one suitable Raman-active organic compound. The components of the solution are then subject to conditions that reduce the metallic cations to form neutral, colloidal metal particles. Since the formation of the metallic colloids occurs in the presence of a suitable Raman-active organic compound, the Raman-active organic compound is readily adsorbed onto the metal during colloid formation. COINs of different sizes can be enriched by centrifugation.

The COINs can include a second metal different from the first metal, wherein the second metal forms a layer overlying the surface of the nanoparticle. To prepare this type of SERS-active nanoparticle, COINs are placed in an aqueous solution containing suitable second metal cations and a reducing agent. The components of the solution are then subject to conditions that reduce the second metallic cations so as to form a metallic layer overlying the surface of the nanoparticle. In certain embodiments, the second metal layer includes metals, such as, for example, silver, gold, platinum, aluminum, and the like. Typically, COINs are substantially spherical and range in size from about 20 nm to 60 nm. The size of the nanoparticle is selected to be about one-half the wavelength of light used to irradiate the COINs during detection.

Typically, organic compounds are attached to a layer of a second metal in COINs by covalently attaching organic compounds to the surface of the metal layer Covalent attachment of an organic layer to the metallic layer can be achieved in a variety ways well known to those skilled in the art, such as for example, through thiol-metal bonds. In alternative embodiments, the organic molecules attached to the metal layer can be crosslinked to form a molecular network.

The COIN(s) can include cores containing magnetic materials, such as, for example, iron oxides, and the like such that the COIN is a magnetic COIN. Magnetic COINs can be handled without centrifugation using commonly available magnetic particle handling systems. Indeed, magnetism can be used as a mechanism for separating biological targets attached to magnetic COIN particles tagged with particular biological probes.

The term "reporter" means a detectable moiety. The reporter can be detected, for example, by Raman spectroscopy. Generally; the reporter and any molecule linked to the reporter can be detected without a second binding reaction. The reporter can be COIN (composite-organic-inorganic nanoparticle), magnetic-COIN, quantum dots, and other Raman or fluorescent tags, for example.

As used herein, "Raman-active organic compound" refers to an organic molecule that produces a unique SERS signature in response to excitation by a laser. A variety of Raman-active organic compounds are contemplated for use as components in COINs. In certain embodiments, Raman-active organic compounds are polycyclic aromatic or heteroaromatic compounds. Typically the Raman-active organic compound has a molecular weight less than about 300 Daltons.

Additional, non-limiting examples of Raman-active organic compounds useful in COINs include TRIT (tetramethyl rhodamine isothiol), NBD (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxytetramethyl amino phthalocyanines, azomethines, cyanines, xanthines, succinylfluoresceins, aminoacridine, and the like.

In certain embodiments, the Raman-active compound is adenine, adenine, 4-amino-pyrazolo(3,4-d)pyrimidine, 2-fluoroadenine, N6-benzolyadenine, kinetin, dimethyl-allyl-amino-adenine, zeatin, bromo-adenine, 8-aza-adenine, 8-azaguanine, 6-mercaptopurine, 4-amino-6-mercaptopyrazolo(3,4-d)pyrimidine, 8-mercaptoadenine, or 9-amino-acridine 4-amino-pyrazolo(3,4-d)pyrimidine, or 2-fluoroadenine. In one embodiment, the Raman-active compound is adenine.

When "fluorescent compounds" are incorporated into COINs, the fluorescent compounds can include, but are not limited to, dyes, intrinsically fluorescent proteins, lanthamide phosphors, and the like. Dyes useful for incorporation into COINs include, for example, rhodamine and derivatives, such as Texas Red, ROX (6-carboxy-X-rhodamine), rhodamine-NHS, and TAMRA (5/6-carboxytetramethyl rhodamine NHS); fluorescein and derivatives, such as 5-bromomethyl fluorescein and FAM (5'-carboxyfluorescein NHS), Lucifer Yellow, IAEDANS, 7-Me$_2$, N-coumarin-4-acetate, 7-OH-4-CH$_3$-coumarin-3-acetate, 7—NH$_2$-4-CH$_3$-coumarin-3-acetate (AMCA), monobromobimane, pyrene trisulfonates, such as Cascade Blue, and monobromotrimethyl-ammoniobimane.

Multiplex testing of a complex sample would generally be based on a coding system that possesses identifiers for a large number of reactants in the sample. The primary variable that determines the achievable numbers of identifiers in currently known coding systems is, however, the physical dimension. Tagging techniques, based on surface-enhanced Raman scattering (SERS) of fluorescent dyes, could be used in the embodiments of this invention for developing chemical structure-based coding systems. The organic compound-assisted metal fusion (OCAM) method could be used to produce composite organic-inorganic nanoparticles (COIN) that are highly effective in generating SERS signals allows synthesis of COIN labels from a wide range of organic compounds to produce sufficient distinguishable COIN Raman signatures to assay any complex biological sample. Thus COIN particles may be used as a coding system for multiplex and amplification-free detection of bioanalytes at near single molecule levels.

COIN particles generate intrinsic SERS signal without additional reagents. Using the OCAMF-based COIN synthesis chemistry, it is possible to generate a large number of different COIN signatures by mixing a limited number of Raman labels for use in multiplex assays in different ratios and combinations. In a simplified scenario, the Raman spectrum of a sample labeled with COIN particles may be characterized by three parameters: (a) peak position (designated as L), which depends on the chemical structure of Raman labels used and the umber of available labels, (b) peak number (designated as M), which depends on the number of labels used together in a single COIN, and (c) peak height (designated as i), which depends on the ranges of relative peak intensity.

The total number of possible distinguishable Raman signatures (designated as T) may be calculated from the following equation:

$$T = \sum_{k=1}^{M} \frac{L!}{(L-k)!k!} P(i,k)$$

where P(i, k)=$i^k$−i+1, being the intensity multiplier which represents the number of distinct Raman spectra that may be generated by combining k (k=1 to M) labels for a given i value. The multiple organic compounds may be mixed in various combinations, numbers and ratios to make the multiple distinguishable Raman signatures. It has been shown that spectral signatures having closely positioned peaks (15 cm$^{-1}$) may be resolved visually. Theoretically, over a million of Raman signatures may be made within the Raman shift range of 500-2000 cm$^{-1}$ by incorporating multiple organic molecules into COIN as Raman labels using the OCAMF-based COIN synthesis chemistry.

Thus, OCAMF chemistry allows incorporation of a wide range of Raman labels into metal colloids to perform parallel synthesis of a large number of COIN labels with distinguishable Raman signatures in a matter of hours by mixing several organic Raman-active compounds of different structures, mixtures, and ratios for use in the invention methods described herein.

COINs may be used to detect the presence of a particular target analyte, for example, a nucleic acid, oligonucleotide, protein, enzyme, antibody or antigen. The nanoclusters may also be used to screen bioactive agents, i.e. drug candidates, for binding to a particular target or to detect agents like pollutants. Any analyte for which a probe moiety, such as a peptide, protein, oligonucleotide or aptamer, may be designed can be used in combination with the disclosed nanoclusters.

Also, SERS-active COINs that have an antibody as binding partner could be used to detect interaction of the Raman-active antibody labeled constructs with antigens either in solution or on a solid support. It will be understood that such immunoassays can be performed using known methods such as are used, for example, in ELISA assays, Western blotting, or protein arrays, utilizing a SERS-active COIN having an antibody as the probe and acting as either a primary or a secondary antibody, in place of a primary or secondary antibody labeled with an enzyme or a radioactive compound. In another example, a SERS-active COIN is attached to an enzyme probe for use in detecting interaction of the enzyme with a substrate.

Another group of exemplary methods could use the SERS-active COINs to detect a target nucleic acid. Such a method is useful, for example, for detection of infectious agents within a clinical sample, detection of an amplification product derived from genomic DNA or RNA or message RNA, or detection of a gene (cDNA) insert within a clone. For certain methods aimed at detection of a target polynucleotide, an oligonucleotide probe is synthesized using methods known in the art. The oligonucleotide is then used to functionalize a SERS-active COIN. Detection of the specific Raman label in the SERS-active COIN identifies the nucleotide sequence of the oligonucleotide probe, which in turn provides information regarding the nucleotide sequence of the target polynucleotide.

The term "complementary" refers to the topological compatibility or matching together of interacting surfaces of a ligand molecule and its receptor. Thus, the receptor and its ligand can be described as complementary, and furthermore, the contact surface characteristics are complementary to each other.

The term "waveguide" refers to a device that controls the propagation of an electromagnetic wave so that the wave is forced to follow a path defined by the physical structure of the guide. Generally speaking, the electric and magnetic fields of an electromagnetic wave have a number of possible arrangements when the wave is traveling through a waveguide. Each of these arrangements is known as a mode of propagation. Optical waveguides are used at optical frequencies. An "optical waveguide" is any structure having the ability to guide optical energy. Optical waveguides may be (a) thin-film deposits used in integrated optical circuits (IOCs) or (b) optical fibers.

The term "optical switch" refers to a switch that enables signals in optical fibers or integrated optical circuits (IOCs) to be selectively switched from one circuit to another. An optical switch may operate by (a) mechanical means, such as physically shifting an optical fiber to drive one or more alternative fibers, or (b) electro-optic effects, magneto-optic effects, or other methods. Slow optical switches, such as those using moving fibers, may be used for alternate routing of an optical transmission path. Fast optical switches, such as those using electro-optic or magneto-optic effects, may be used to perform logic operations. One type of an optical switch is a thin film optical switch, which is a switch having multilayered films of material of different optical characteristics, that is capable of switching transmitted light by using electro-optic, electro-acoustic, or magneto-optic effects to obtain signal switching, and is usually used as a component in integrated optical circuits. Thin-film optical switches may support primarily one propagation mode.

The term "PIN diode" refers to positive-intrinsic-negative diode. A photodiode with a large, neutrally doped intrinsic region sandwiched between p-doped and n-doped semiconducting regions. A PIN diode exhibits an increase in its electrical conductivity as a function of the intensity, wavelength, and modulation rate of the incident radiation. A PIN diode is also called photodiode.

The terms "spectrum" or "spectra" refer to the intensities of electromagnetic radiation as a function of wavelength or other equivalent units, such as wavenumber, frequency, and energy level.

The term "spectrometer" refers to an instrument equipped with scales for measuring wavelengths or indexes of refraction.

The term "dispersive spectrometer" refers to a spectrometer that generates spectra by optically dispersing the incoming radiation into its frequency or spectral components. Dispersive spectrometers can be further classified into two types: monochromators and spectrographs. A monochromator uses a single detector, narrow slit(s) (usually two, one at the entrance and another at the exit port), and a rotating dispersive element allowing the user to observe a selected range of wavelength. A spectrograph, on the other hand, uses an array of detector elements and a stationary dispersive element. In this case, the slit shown in the figure is removed, and spectral elements over a wide range of wavelengths are obtained at the same time, therefore providing faster measurements with a more expensive detection system.

The term "dispersive element" refers to a component of a dispersive spectrometer that can disperse electromagnetic radiation such a light. Dispersive elements include prisms and gratings.

The term "interferometer" refers to an instrument that uses the principle of interference of electromagnetic waves for purposes of measurement. For example, it could be any of several optical, acoustic, or radio frequency instruments that use interference phenomena between a reference wave and an experimental wave or between two parts of an experimental wave to determine wavelengths and wave velocities, measure very small distances and thicknesses, and calculate indices of refraction.

The term "non-dispersive element" refers to an interferometer that does not disperse electromagnetic radiation in spatial domain but instead creates a phase shift in the electromagnetic radiation.

The term "Fourier transform spectrometer" refers to a spectrometer used for Fourier transform spectroscopy, which is a measurement technique whereby spectra are collected based on the response from a pulse of electromagnetic radiation. It can be applied to variety of types of spectroscopy including infrared spectroscopy (FTIR), nuclear magnetic resonance, and electron spin resonance spectroscopy. Fourier transform spectroscopy can be more sensitive and has a much shorter sampling time than conventional spectroscopic techniques. For example, in a conventional (or "continuous wave") nucleic magnetic resonance spectrometer, a sample is exposed to electromagnetic radiation and the response (usually the intensity of transmitted radiation) is monitored. The energy of the radiation is varied over the desired range and the response is plotted as a function of radiation energy (or frequency). At certain resonant frequencies characteristic of the specific sample, the radiation will be absorbed resulting in a series of peaks in the spectrum, which can then be used to identify the sample. (In magnetic spectroscopy, the magnetic field is often varied instead of the frequency of the incident radiation, though the spectra are effectively the same as if the field had been kept constant and the frequency varied. This is largely a question of experimental convenience.) Instead of varying the energy of the electromagnetic radiation, Fourier Transform nucleic magnetic resonance spectroscopy exposes the sample to a single pulse of radiation and measures the response. The resulting signal, called a free induction decay, contains a rapidly decaying composite of all possible frequencies. Due to resonance by the sample, resonant frequencies will be dominant in the signal and by performing a mathematical operation called a Fourier transform on the signal the frequency response can be calculated. In this way the Fourier transform nucleic magnetic resonance spectrometer can produce the same kind of spectrum as a conventional spectrometer, but generally in a much shorter time.

The term "interferogram" or "Fourier transform spectrum" used herein means the detector response of a single channel detector or a low-density detector as a function of the optical path length difference caused by the interference of electromagnetic radiation.

The term "operably coupled" means that there is a functional interaction between two or more units of an apparatus and/or system. For example, a Raman detector may be "operably coupled" to a flow through cell (sample stage), nanochannel, microchannel, or microfluidic channel, if for example the Raman detector is arranged so that it can detect single molecule samples such as analytes, such as nucleotides, as they pass through the sample stage, nanochannel, microchannel, or microfluidic channel. Also for example a Raman detector may be "operably coupled" to a computer if for example the computer can obtain, process, store and/or transmit data on Raman signals detected by the Raman detector.

The term "analyte" means any atom, chemical, molecule, compound, composition or aggregate of interest for detection and/or identification. Examples of analytes include, but are not limited to, an amino acid, peptide, polypeptide, protein, glycoprotein, lipoprotein, nucleoside, nucleotide, oligonucleotide, nucleic acid, sugar, carbohydrate, oligosaccharide, polysaccharide, fatty acid, lipid, hormone, metabolite, cytokine, chemokine, receptor, neurotransmitter, antigen, allergen, antibody, substrate, metabolite, cofactor, inhibitor, drug, pharmaceutical, nutrient, prion, toxin, poison, explosive, pesticide, chemical warfare agent, biohazardous agent, radioisotope, vitamin, heterocyclic aromatic compound, carcinogen, mutagen, narcotic, amphetamine, barbiturate, hallucinogen, waste product and/or contaminant. In certain embodiments of the invention, one or more analytes may be labeled with one or more Raman labels, as disclosed below. The sample such as an analyte in the embodiments of this invention could be in the form of solid, liquid or gas. The sample could be analyzed by the embodiments of the method and device of this invention when the sample is at room temperature and at lower than or higher than the room temperature.

The term "label" is used to refer to any atom, molecule, compound or composition that can be used to identify a sample such as an analyte to which the label is attached. In various embodiments of the invention, such attachment may be either covalent or non-covalent. In non-limiting examples, labels may be fluorescent, phosphorescent, luminescent, electroluminescent, chemiluminescent or any bulky group or may exhibit Raman or other spectroscopic characteristics.

A "Raman label" may be any organic or inorganic molecule, atom, complex or structure capable of producing a detectable Raman signal, including but not limited to synthetic molecules, dyes, naturally occurring pigments such as phycoerythrin, organic nanostructures such as $C_{60}$, buckyballs and carbon nanotubes, metal nanostructures such as gold or silver nanoparticles or nanoprisms and nano-scale semiconductors such as quantum dots. Numerous examples of Raman labels are disclosed below. A person of ordinary skill in the art will realize that such examples are not limiting, and that "Raman label" encompasses any organic or inorganic atom, molecule, compound or structure known in the art that can be detected by Raman spectroscopy.

The term "nanocrystalline silicon" refers to silicon that comprises nanometer-scale silicon crystals, typically in the size range from 1 to 100 nanometers (nm).

The term "porous silicon" refers to silicon that has been etched or otherwise treated to form a porous structure.

The term "fluid" used herein means an aggregate of matter that has the tendency to assume the shape of its container, for example a liquid or gas. Analytes in fluid form can include fluid suspensions and solutions of solid particle analytes.

When light passes through a medium of interest, a certain amount becomes diverted from its original direction. This phenomenon is known as scattering. Some of the scattered light differs in frequency from the original excitatory light, due to a) the absorption of light by the medium, b) excitation of electrons in the medium to a higher energy state, and c) subsequent emission of the light from the medium at a different wavelength. When the frequency difference matches the energy level of the molecular vibrations of the medium of interest, this process is known as Raman scattering. The wavelengths of the Raman emission spectrum are characteristic of the chemical composition and structure of the molecules absorbing the light in a sample, while the intensity of light scattering is dependent on the concentration of molecules in the sample as well as the structure of the molecule.

Typically, the probability of Raman interaction occurring between an excitatory light beam and an individual molecule in a sample is very low, resulting in a low sensitivity. The term "optical cross section" indicates the probability of an optical event occurring in a particular molecule or a particle. When photons impinge on a molecule, only some of the photons that geometrically impinge on the molecule interact with the electron cloud of the molecule. The term "geometric cross-section" is the volume per molecule in which the photons interact with the electron cloud of the molecule. The term "cross section" is the product of the geometric cross-section and the optical cross section. Optical detection and spectroscopy techniques of a single molecule require cross sections greater than $10^{-21}$ cm$^2$/molecule, more preferably cross-sections greater than $10^{-16}$ cm2/molecule. On the other hand, typical spontaneous Raman scattering techniques have cross sections of about $10^{-30}$ cm2/molecule, and thus are not suitable for single molecule detection.

The embodiments of the invention are directed to improved SERS and SECARS devices and method of manufacturing and using the same. In one embodiment of the invention, a device having at least one laser, a sample stage and a detector, wherein the sample stage is moveable and has a SERS active material is disclosed. In another embodiment of the invention, the device has at least one laser, a scanning mirror, a sample stage having a SERS active material and a detector, wherein the scanning mirror is adapted to steer a laser beam across a surface of the sample stage. The device could further comprise a lens such as a microscope objective or at least one mirror that is adapted to function as a lens. Preferably, the device is adapted to produce at least two laser beams of different wavelengths. The device could further comprise a dichroic mirror that is adapted to produce spatial overlap of said at least two laser beams and an autocorrelator adapted to monitor temporal overlap of said at least two laser beams. The device could further comprise at least two lasers. The device could further comprise a phase lock adapted to compare laser pulses generated by said at least two lasers. The device could further comprise a dispersive spectrograph or a non-dispersive spectrograph. Preferably, the sample stage is moveable in X, Y and Z directions. The device could further comprise a scanning mirror adapted to steer a laser beam across a surface of the sample stage, an optical parametric oscillator adapted to produce at least one laser beam, an optical parametric oscillator adapted to produce at least two laser beams, a laser line filter, a half-waveplate, a bandpass filter and/or a polarizer.

Other embodiments of the invention include a method of manufacturing a device comprising placing at least one laser, placing a sample stage and placing a detector, wherein the sample stage is moveable and comprises a SERS active material. The method could further comprise placing a lens in a path of a laser beam in the device, placing a dichroic mirror that is adapted to produce spatial overlap of said at least two laser beams, placing an autocorrelator that is adapted to monitor temporal overlap of said at least two laser beams, placing a phase lock that is adapted to compare laser pulses generated by said at least two lasers, placing a dispersive spectrograph, placing a non-dispersive spectrograph, placing a scanning mirror that is adapted to steer a laser beam across a surface of the sample stage, placing an optical parametric oscillator that is adapted to produce at least one laser beam, placing an optical parametric oscillator adapted to produce at least two laser beams, placing a laser line filter and/or a half-waveplate in a path of a laser beam, and/or placing a bandpass filter and/or a polarizer in a path of a laser beam.

Other embodiments of the invention relate to a method of imaging comprising a SECARS equipment, the method comprising forming at least two laser beams of different wavelengths, creating a spatial overlap of said at least two laser beams, and creating a temporal overlap of said at least two laser beams, directing said at least two laser beams on a surface of a sample stage comprising a SERS active material, monitoring a wavelength of said at least two laser beams, tuning said at least two laser beams, monitoring a pulse width of said at least two laser beams, engaging a phase lock so that a phase delay between said at least two laser beams is contact, moving a sample placed on the sample stage or steering said at least two laser beams across the sample, collecting a SECARS signal and/or processing the SECARS signal to identify the sample.

SECARS is a physical process combining surface enhanced Raman scattering (SERS) and coherent anti-Stokes Raman scattering (CARS). In SERS, molecules located near metal are excited by the surface plasmon generated by interaction between the excitation light and the metallic surface. Specifically, it has been observed that molecules near roughened silver surfaces show enhanced Raman scattering of as much as six to seven orders of magnitude. The SERS effect is related to the phenomenon of plasmon resonance, wherein a metal surface exhibits a pronounced optical resonance in response to incident electromagnetic radiation, due to the collective coupling of conduction electrons in the metal. In essence, metal surface can function as miniature "antenna" to enhance the localized effects of electromagnetic radiation. Molecules located in the vicinity of such surfaces exhibit a much greater sensitivity for Raman spectroscopic analysis. In ideal condition, the surface plasmon has several orders of magnitude higher intensity of electromagnetic field compared to the intensity of electromagnetic field of excitation light, and hence the Raman scattering by the molecules are several orders stronger than what the excitation light would have generated without the surface enhancements.

SERS is usually accomplished by using either rough metal films which are attached to a substrate as part of the sample stage of the spectroscopic measuring device or by introducing metallic nanoparticles or colloids as part of a suspension into the sample stage. The sample is then applied to these metal surfaces. SERS techniques can give strong intensity enhancements by a factor of up to $10^{14}$ to $10^{16}$, but only for certain molecules (for example, dye molecules, adenine, hemoglobin, and tyrosine), which is near the range of single molecule detection.

Generally, SERS is observed for molecules found close to silver or gold nanoparticles (although other metals may be used, but with a reduction in enhancement). The mechanism by which the enhancement of the Raman signal is provided is from a local electromagnetic field enhancement provided by an optically active nanoparticle. Current understanding suggests that the enhanced optical activity results from the excitation of local surface plasmon modes that are excited by focusing laser light onto the nanoparticle. SERS gives all the information usually found in Raman spectra; it is a sensitive vibrational spectroscopy that gives structural information on the molecule and its local interactions.

Coherent anti-Stokes Raman spectroscopy (CARS) is a third-order nonlinear optical process involving a pump and a Stokes laser beam that interacts with the sample and generates an anti-Stokes field. The latter is resonantly enhanced when the difference in photon energies coincides with the frequency of a Raman resonance, which provides the intrinsic vibrational contrast mechanism. Typically, two lasers beams whose frequency difference is selected to match the vibrational energy of the target molecule are used to generate four-wave-mixing. In the presence of the molecule whose vibrational energy level matches the frequency difference between the two laser beams, light of a third frequency is produced.

In some sense, the fundamental optical phenomenon resulting in a CARS signal is not really Raman spectroscopy, because the third-order phenomenon produces a weak signal considered as a three-photon interaction of virtual states, as in multi-photon microscopy. However, the strength of the signal is greatly increased when the difference in energy of the virtual state correspond to the vibrational energy of a Raman-active state, which is why CARS has its special name. This amplification is typically the vibrational contrast mechanism, and the (usually spatially-resolved) CARS signal observed corresponds to the presence (and concentration) of species which are Raman-active at the frequency in question, the difference between the pump beam and the Stokes beam frequencies.

Typically, coherent anti-Stokes Raman scattering (CARS) is a four-wave mixing process which uses a pump beam or wave of Raman light in combination with a Stokes beam, with center frequencies at $\omega_p$ and $\omega_s$, respectively. When $\omega_p$-$\omega_s$ is tuned to be resonant with a given vibrational mode in a molecule, a CARS signal of enhanced intensity is observed from the resultant scattered light at the anti-Stokes frequency of $2\omega_p$-$\omega_s$. Unlike spontaneous Raman scattering, CARS is highly sensitive and can be detected in the presence of background fluorescence induced by one-photon excitation. CARS techniques give intensity enhancement by a factor of about $10^5$ which yields cross sections in the range of about $10^{-25}$ cm$^2$/molecule, still too small for optical detection and spectroscopy of single molecules.

By the embodiments of this invention, CARS and SERS techniques could be combined such that cross sections of up to about $10^{-21}$ to $10^{-16}$ cm$^2$/molecule could be consistently observed for a wide range of molecules. Enhancements in this range would consistently be in the range of single molecule detection. The combination of SERS and CARS, surface enhanced coherent anti-Stokes Raman spectroscopy (hereinafter SECARS) by the embodiments of this invention allows for single molecule detection. To achieve SECARS enhancements by a factor of $10^9$ to $10^{18}$ or greater, the particular conditions should preferably be finely tuned for each type of molecule.

Surface-Enhanced Coherent Anti-Stokes Raman Spectroscopy

The SECARS device and method of the embodiments of the invention involve launching both a Stokes light and a pump light of different Raman wavelengths at a target area defined by the interface between the molecules to be detected and/or identified and a Raman active surface. In one embodiment, a Raman active surface could be operably coupled to one or more Raman detection units.

Figure 2:
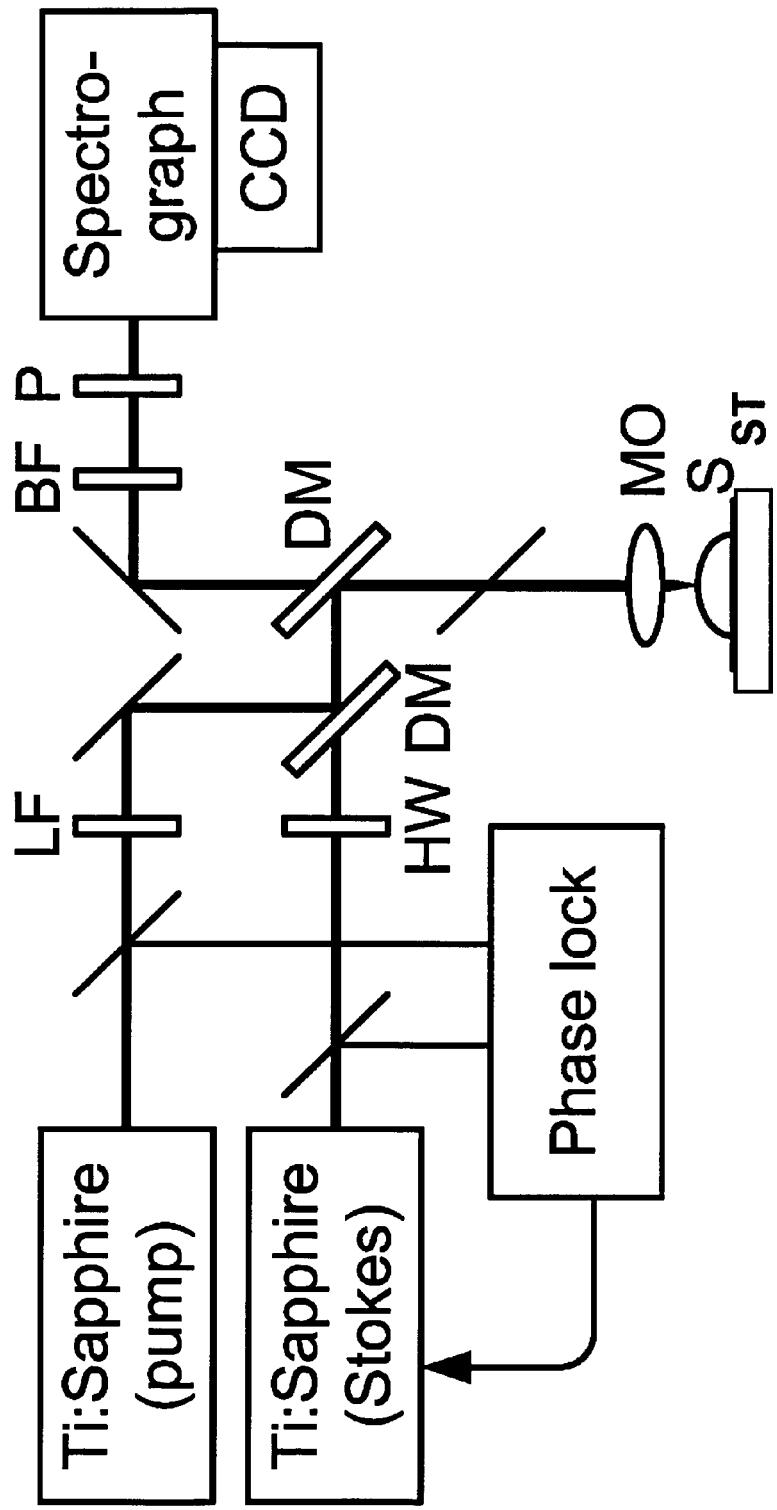
FIGS. 2-8 shows different embodiments of an improved SECARS device of this invention.

One embodiment of the SECARS device of this invention is shown in FIG. 2. Two picoseconds Ti:sapphire lasers, each generating 3 picoseconds pulses at 76 MHz repetition rate, are synchronized by a phase-locking device (SynchroLock AP, Coherent, Santa Clara, Calif.). The polarization of the Stokes laser is modulated by a half-waveplate (HW) while the pump laser passes though a laser line filter (LF). The two laser pulses from the Stokes and pump lasers are overlapped by a dichroic mirror (DM). The overlapped beam is focused onto a sample (S) by a microscope objective (MO). The back-scattered SECARS signal is collected by the same microscope objective, and both laser lines are blocked by a band-pass filter (BF). The filtered light is sent to a spectrometer via a polarizer (P), where the dispersion of light is recorded by a charge coupled device (CCD) camera, preferably a cooled CCD camera. The temporal overlap of laser pulses is monitored by the autocorrelator.

Figure 3:
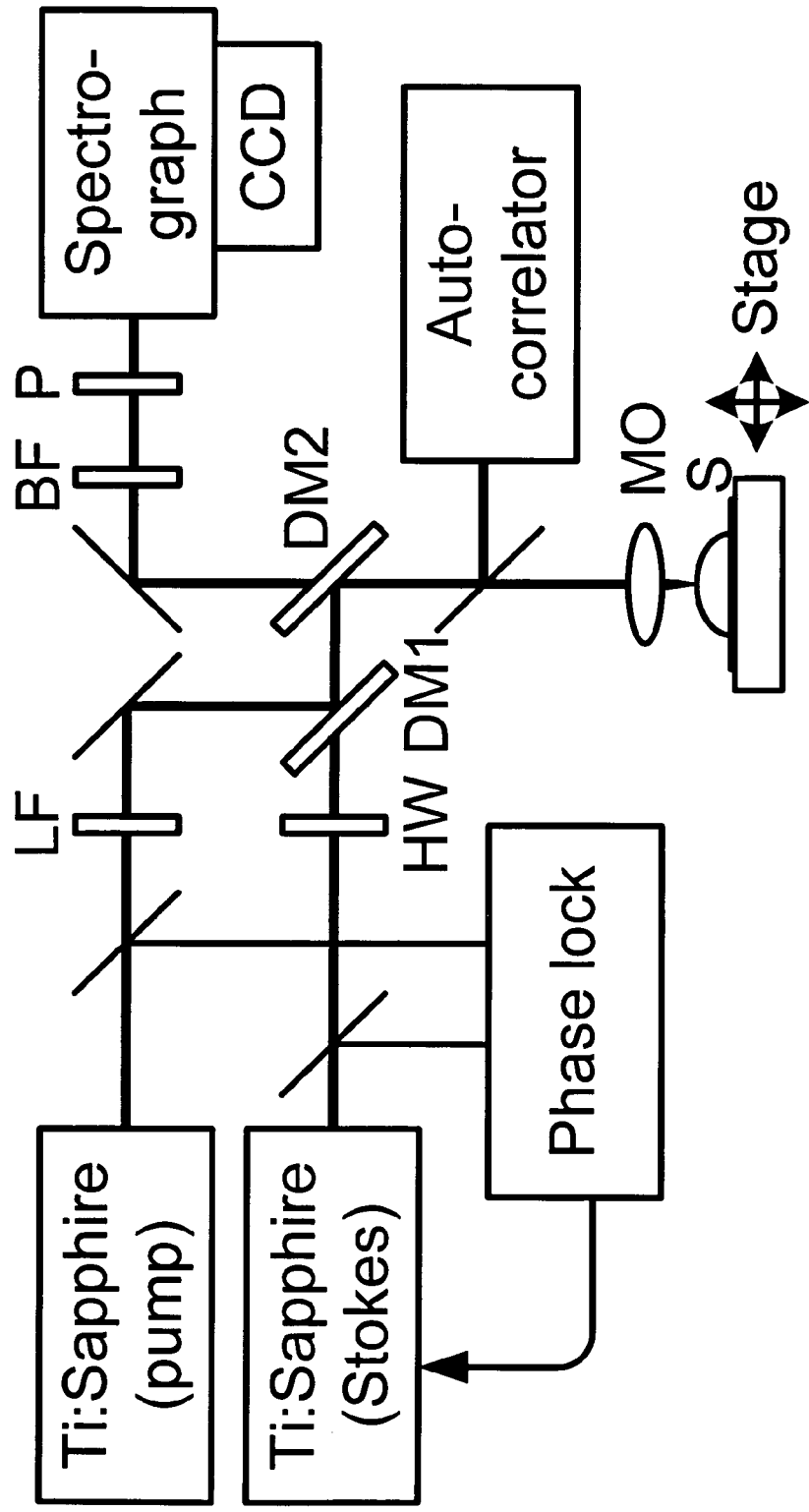
Figure 4:
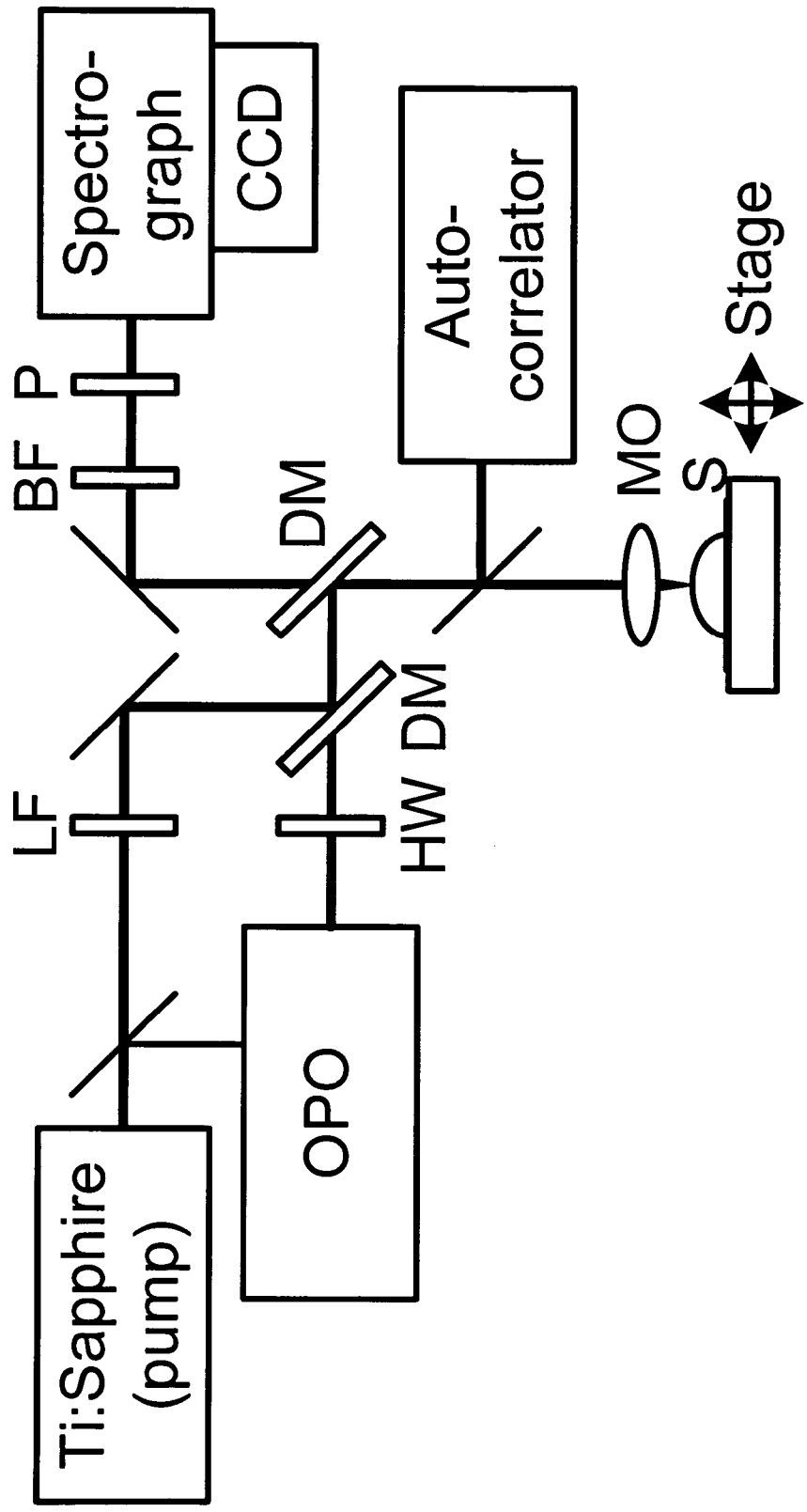
Figure 5:
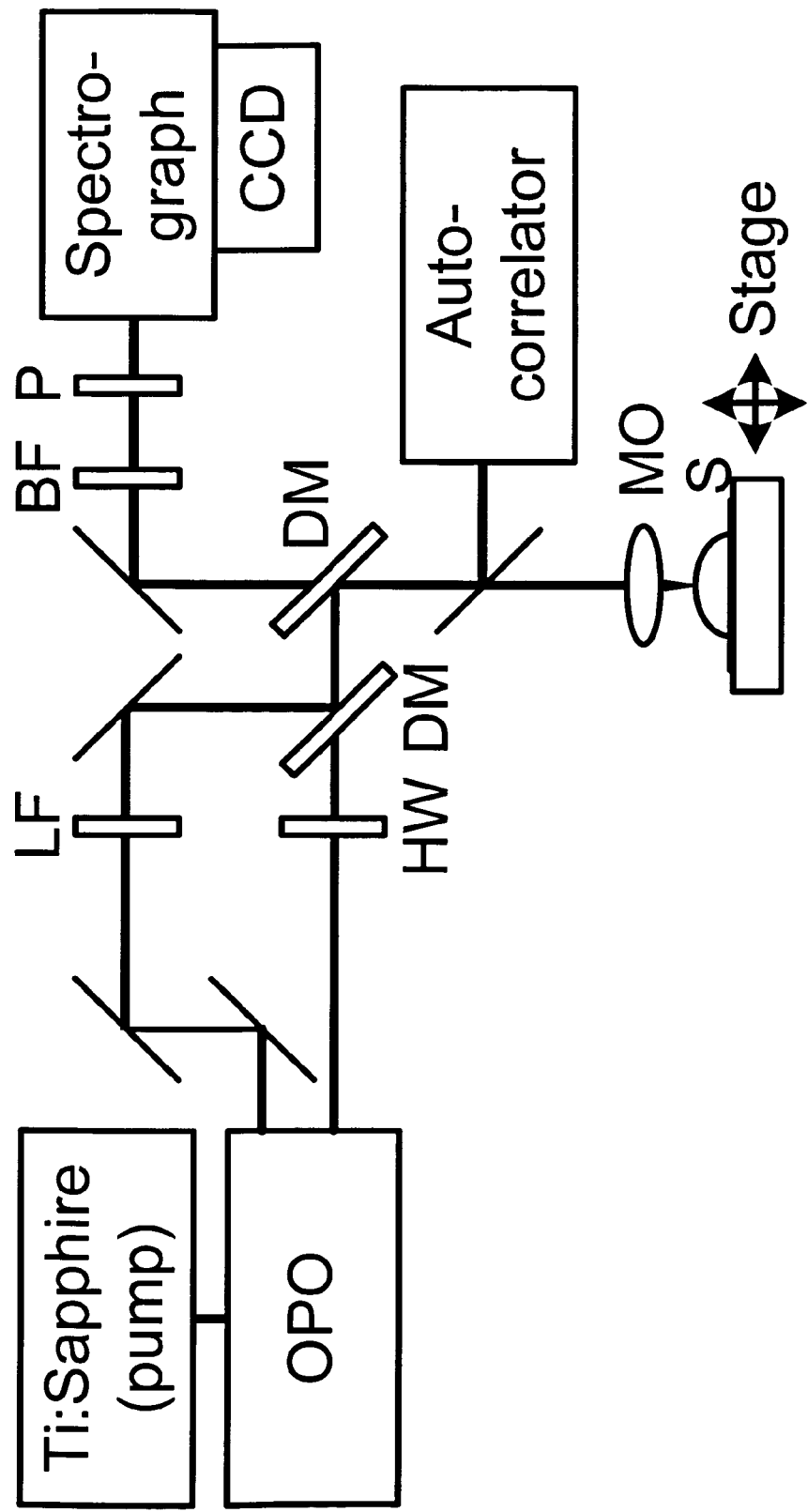

In the embodiments of the invention, the Stokes laser and the pump laser could be generated in at least three distinct ways: (a) by using two lasers that are synchronized by a phase-locking device as shown in FIGS. 2 and 3; (b) by using one laser and an optical parametric oscillator (OPO) to generate the second laser beam as shown in FIG. 4; and (c) by using one laser and an OPO to generate two laser beams as shown in FIG. 5.

Figure 6:
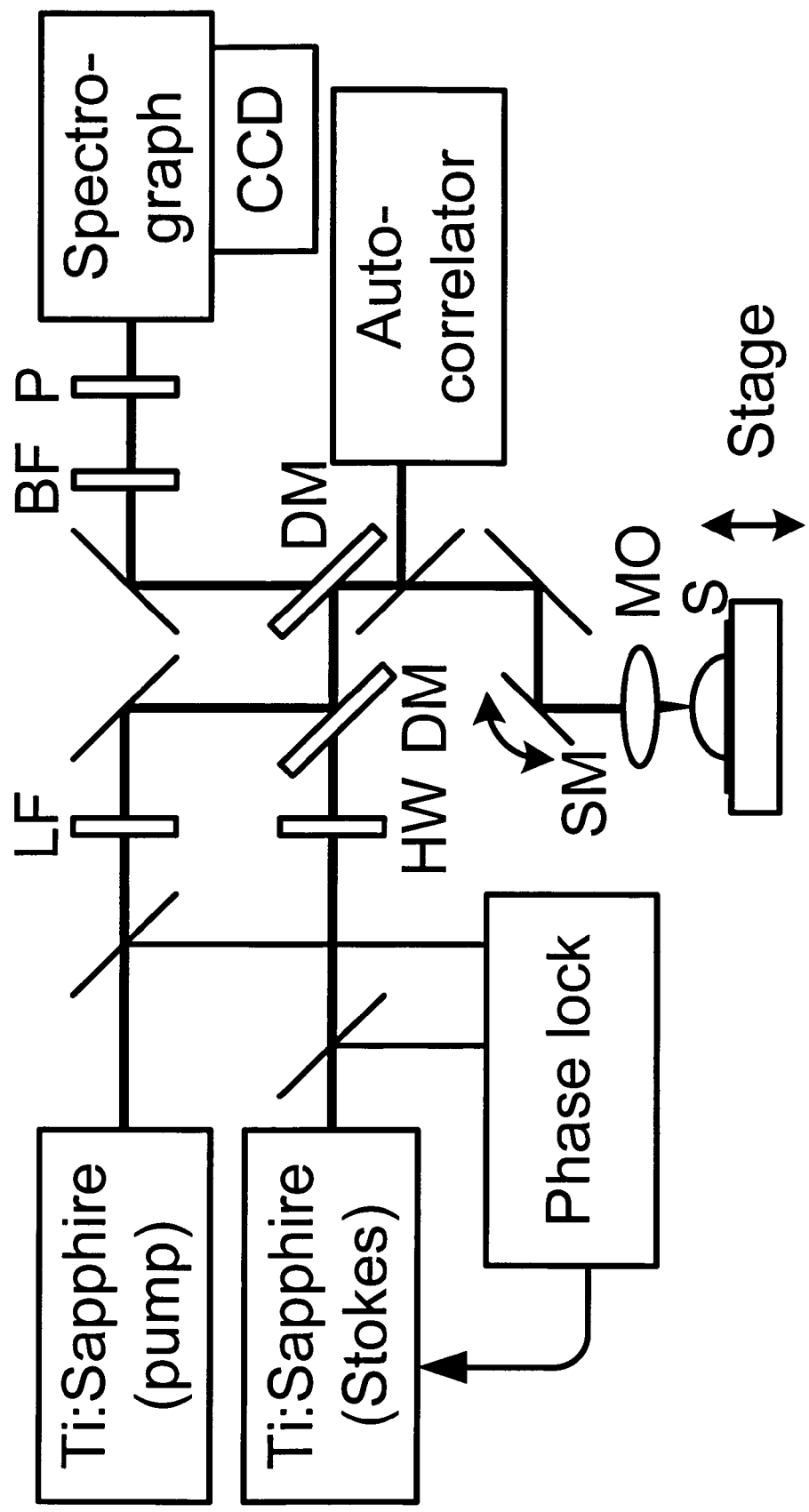

In the embodiments of the invention, the scanning of the sample could be done in at least two distinct ways: (a) systematically moving the sample stage as shown in FIGS. 3-5, 7 and 8 and (b) steering the beam through the body of the sample using a scanning mirror as shown in FIG. 6.

Figure 7:
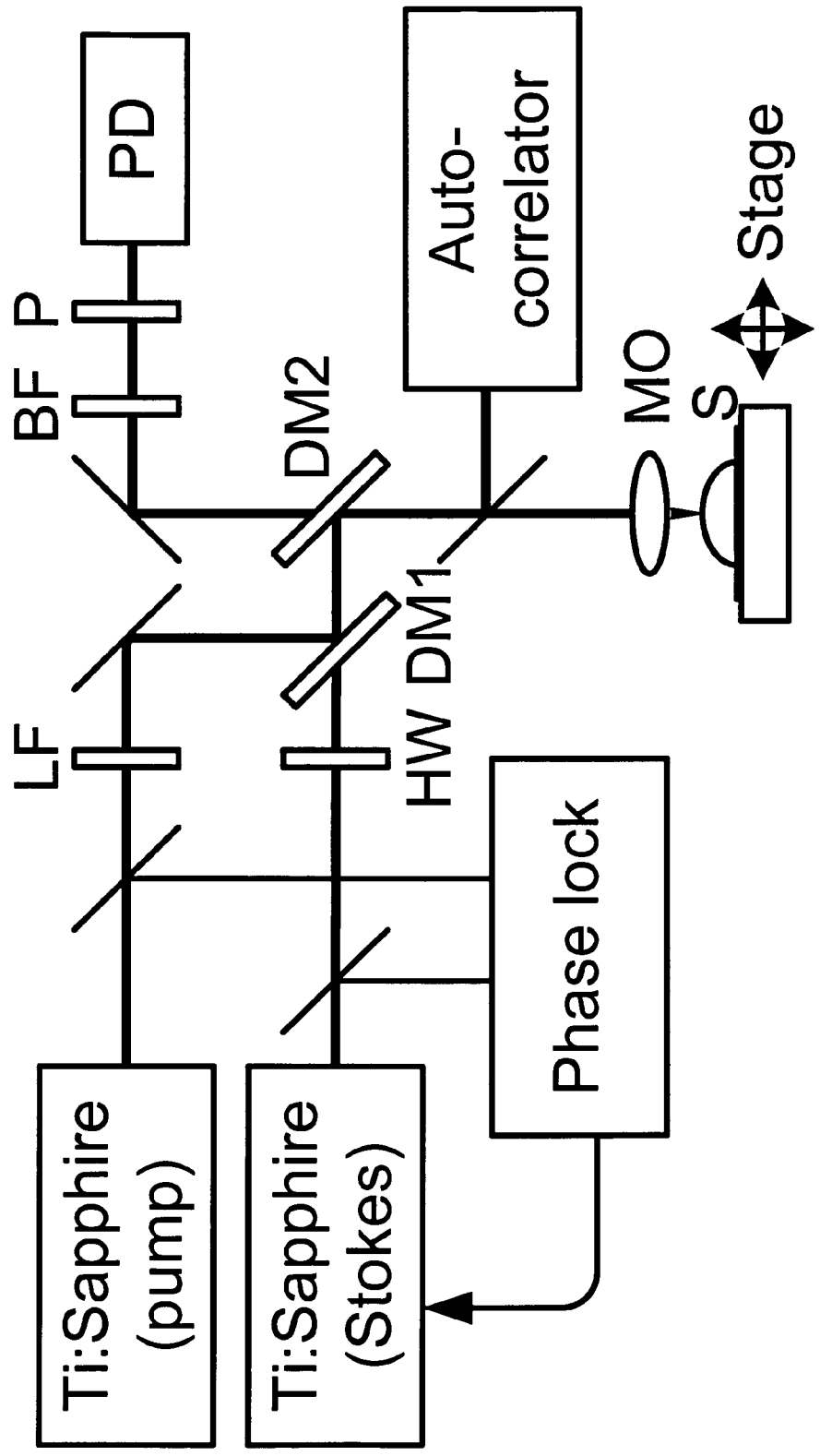
Figure 8:
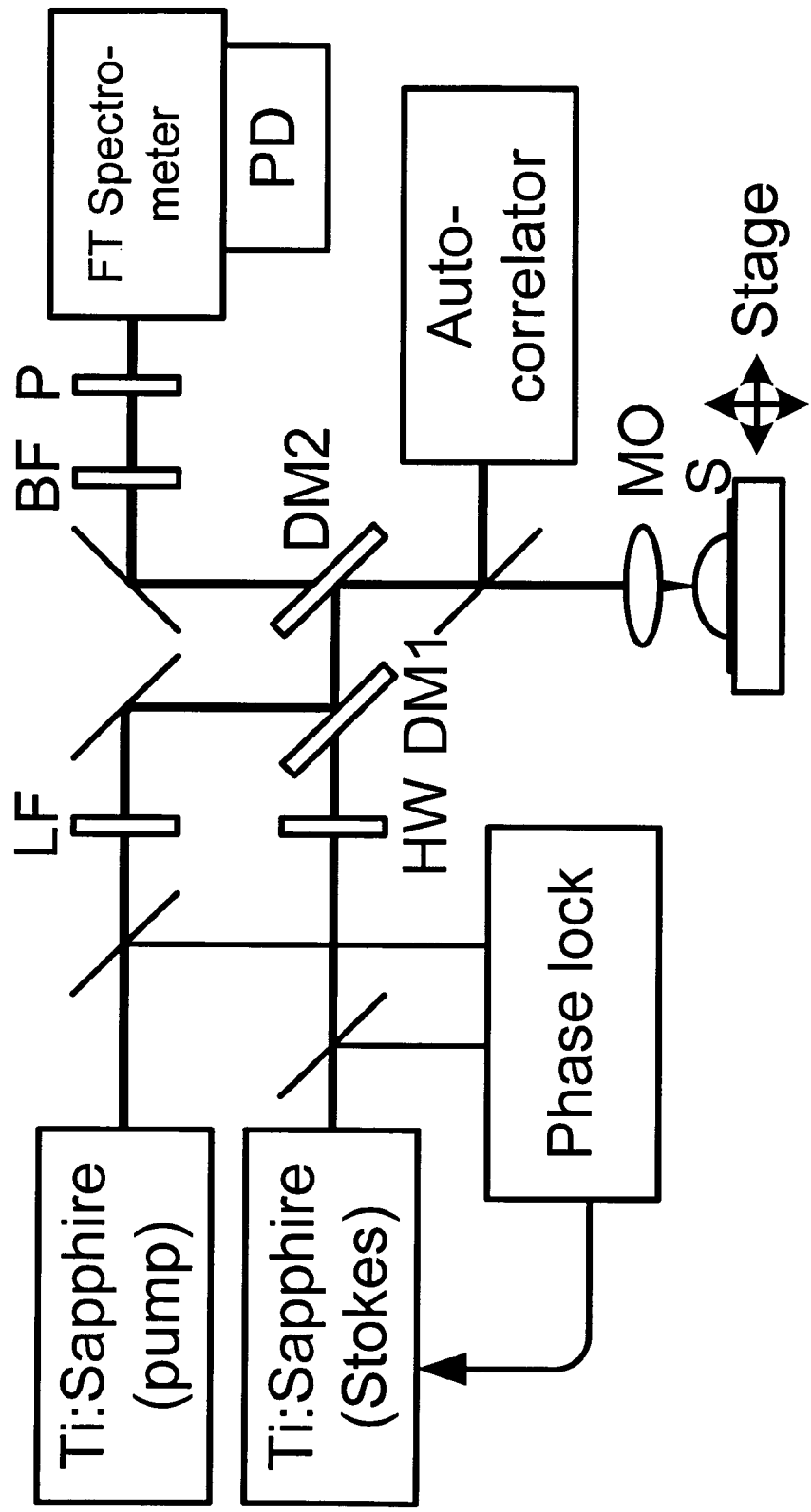

In the embodiments of the invention, the detection of the Raman signal could be done in at least three ways: (a) using a combination of a dispersive spectrometer and a CCD camera as shown in FIGS. 2-6; (b) using a single channel detector or a low-density detector such as a photodiode, a photomultiplier tube, or an avalanche photodiode as shown in FIG. 7; and (c) using a combination of a non-dispersive spectrometer such as a Fourier transform spectrometer in combination with a single channel detector or a low-density detector such as a photodiode, a photomultiplier tube, or an avalanche photodiode as shown in FIG. 8.

By the embodiments of this invention, the combination of the SERS and CARS process generates even stronger signal, stronger than what can be achieved by SERS or CARS alone, and that the sensitivity of the combined technique, SECARS, is such that it can even detect single molecules that could not be detected by SERS or CARS alone.

The signal strength of surface enhanced CARS depends on the strength of the input pump beam; however, the maximum laser intensity on the interface is often limited by optical damage. For this reason, it is preferable to use a shorter pump pulsed laser beam which has a high peak power than a typical continuous-wave laser beam. Continuous wave (CW) lasers typically provide microwatts to a watt at high peak power levels, whereas pulsed lasers provide kilowatts to gigawatts at high peak power levels when operated at the same average power. This yields stronger signals which remain below the optical damage threshold. The width of the pulses ranges from about 100 nanoseconds to about 80 femtoseconds. Typically, the pulse widths of from about 100 femtoseconds to about seven picoseconds yield the best results, depending on the peak power and the spectral line width of the beam.

Pulsed laser beams or CW laser beams may be used. When a laser is used, the input beams should be synchronized to guarantee overlap of the beams. This may be accomplished by a suitable laser controller or other type of synchronization electronics. Examples of commercially available electronics that may be used include, but are not limited to, a Lok-to-Clock device (Spectra-Physics) or a SynchroLock device (Coherent). These electronic devices may require additional photodiodes and beam splitters for their operation, which are not depicted in FIG. 2. An alternative embodiment uses an optical parametric oscillator (OPO), which takes a single laser beam input and generates two synchronized beams at different tunable wavelengths.

The wave vector of the pump wave can be adjusted to satisfy the surface phase-matching condition:

$$2k_1 - k_2 = k_a(\omega_a) = K'(\omega_a)$$

wherein $k_1$ is the wave vector of the first beam; $k_2$ is the wave vector of the second beam; $k_a(\omega_a)$ is the wave vector of the anti-Stokes signal; and $K'(\omega_a)$ is the wavevector of the surface EM wave.

The microscope objective (MO) of FIG. 2 focuses the light onto a sample placed on or within a sample stage. The light is focused into a region which contains molecules of the sample such as an analyte to be detected surrounded by a Raman active surface, which could be of various forms. For example, Raman active surfaces include, but are not limited to: a metallic surface, such as one or more layers of nanocrystalline and/or porous silicon coated with a metal or other conductive material; a particle, such as a metallic nanoparticle; an aggregate of particles, such as a metallic nanoparticle aggregate; a colloid of particles (with ionic compounds), such as a metallic nanoparticle colloid; or combinations thereof.

The anti-Stokes beam of radiation emitted by the sample and magnified by the Raman active surface passes out of the sample stage and travels as a coherent beam that is collected by the confocal or standard optics and optionally coupled to a monochromator for spectral dissociation. The beam is detected with a Raman detector unit, typically a spectrometer. The highly directional output of the anti-Stokes beam allows for its detection even in the presence of a strongly luminescent background.

The CCD camera in FIG. 2 is a Raman detection unit, which can be any generic optical detector with sufficient sensitivity and speed to detect small numbers of molecules of a particular sample. Sensitivity comparable to that of cooled, CCD arrays is sufficient. The speed of detection is within milliseconds to nanoseconds in range. The Raman detection unit may comprise a large or small area detector, an array of detectors, or the like. Examples of such detectors include photodiodes, avalanche-photodiodes, CCD arrays, complementary metal oxide semiconductor (CMOS) arrays, intensified CCDs, and the like. CCD, CMOS, and avalanche photodiodes are preferred. The detector of the Raman detection unit generates electrical output signals indicative of the variation of intensity of light with position across the anti-Stokes wave or beam; the SECARS effect dictating that strong absorption will occur at a particular angle or intensity as determined by material in the sample being tested. These electrical signals are sampled/counted and digitized and fed via associated circuitry (not shown in FIG. 2) to a suitable data analyzing arrangement which may include a information processing and control system or computer.

Examples of a Raman detection unit include, but are not limited to, a Spex Model 1403 double-grating spectrophotometer with a gallium-arsenide photomultiplier tube operated as a single-photon counting model (RCA Model C31034 or Burle Indus. Model C3103402); an ISA HR-320 spectrograph equipped with a red-enhanced intensified charge-coupled device (RE-ICCD) detection system (Princeton Instruments); Fourier-transform spectrographs (based on Michaelson interferometers), charged injection devices; photodiode arrays, including avalanche photodiode arrays; InGaAs detectors; electron-multiplied CCD; intensified CCD and/or phototransistor arrays.

In certain embodiments of the invention, the apparatus may comprise an information processing system or computer. The disclosed embodiments are not limiting for the type of information processing system or computer used. An exemplary information processing system or computer may comprise a bus for communicating information and a processor for processing information. The information processing and control system or computer may further comprise a random access memory (RAM) or other dynamic storage device, a read only memory (ROM) or other static storage and a data storage device such as a magnetic disk or optical disc and its corresponding drive. The information processing and control system or computer may further comprise any peripheral devices known in the art, such as memory, a display device (e.g., cathode ray tube or Liquid Crystal Display (LCD)), an alphanumeric input device (e.g., keyboard), a cursor control device (e.g., mouse, trackball, or cursor direction keys) and a communication device (e.g., modem, network interface card, or interface device used for coupling to Ethernet, token ring, or other types of networks).

Data from the detection unit may be processed by the processor and data stored in the memory, such as the main memory. Data on emission profiles for standard samples may also be stored in memory, such as main memory or in ROM. For example, the processor may compare the emission spectra from the sample molecules and the Raman active surface to identify the type of analyte(s) in the sample(s). For example, the information processing system may perform procedures such as subtraction of background signals and "base-calling" determination when overlapping signals are detected as part of nucleotide identification. It is appreciated that a differently equipped computer may be used for certain implementations. Therefore, the configuration of the system may vary in different embodiments of the invention.

While the methods disclosed herein may be performed under the control of a programmed processor, in alternative embodiments of the invention, the processes may be fully or partially implemented by any programmable or hardcoded logic, such as Field Programmable Gate Arrays (FPGAs), TTL logic, or Application Specific Integrated Circuits (ASICs), for example. Additionally, the disclosed methods may be performed by any combination of programmed general purpose computer components and/or custom hardware components.

Following the data gathering operation, the data will typically be reported to a data analysis operation. To facilitate the analysis operation, the data obtained by the detection unit will typically be analyzed using a digital computer such as that described above. Typically, the computer will be appropriately programmed for receipt and storage of the data from the detection unit as well as for analysis and reporting of the data gathered.

In certain embodiments of the invention, custom designed software packages may be used to analyze the data obtained from the detection unit. In alternative embodiments of the invention, data analysis may be performed, using an information processing system or computer and publicly available software packages. Non-limiting examples of available software for DNA sequence analysis include the PRISM™ DNA Sequencing Analysis Software (Applied Biosystems, Foster City, Calif.), the Sequencherm package (Gene Codes, Ann Arbor, Mich.), and a variety of software packages available through the National Biotechnology Information Facility at website www.nbif.org/links/1.4.1.php.

Raman-Active Surfaces (a) Nanoparticles, Aggregates, and Colloids

In certain embodiments of the invention, the Raman active surface is provided by metal nanoparticles, which may used alone or in combination with other Raman active surfaces, such as a metal-coated porous silicon substrate to further enhance the Raman signal obtained from small numbers of molecules of a sample such as an analyte. In various embodiments of the invention, the nanoparticles are silver, gold, platinum, copper, aluminum, or other conductive materials, although any nanoparticles capable of providing a SECARS signal may be used. Particles made of silver or gold are especially preferred.

The particles or colloid surfaces can be of various shapes and sizes. In various embodiments of the invention, nanoparticles of between 1 nanometer (nm) and 2 micrometers (micron) in diameter may be used. In alternative embodiments of the invention, nanoparticles of 2 nm to 1 micron, 5 nm to 500 nm, 10 nm to 200 nm, 20 nm to 100 nm, 30 nm to 80 nm, 40 nm to 70 nm or 50 nm to 60 nm diameter may be used. In certain embodiments of the invention, nanoparticles with an average diameter of 10 to 50 nm, 50 to 100 nm or about 100 nm may be used. If used in combination with another Raman active surface, such as a metal-coated porous silicon substrate, the size of the nanoparticles will depend on the other surface used. For example, the diameter of the pores in the metal-coated porous silicon may be selected so that the nanoparticles fit inside the pores.

The nanoparticles may be approximately spherical, cylindrical, triangular, rod-like, edgy, multi-faceted, prism, or pointy in shape, although nanoparticles of any regular or irregular shape may be used. In certain embodiments of the invention, the nanoparticles may be single nanoparticles, and/or random colloids of nanoparticles (optionally with ionic compounds). Colloids of nanoparticles are synthesized by standard techniques, such as by adding ionic compounds, such as NaCl, to the nanoparticles. The aggregation can be induced by the "depletion mechanism," wherein the addition of non-adsorbing nanoparticles effectively results in an attraction potential due to the depletion of the nanoparticles from the region between two closely approaching nanoparticles.

In other embodiments of the invention, nanoparticles may be cross-linked to produce particular aggregates of nanoparticles, such as dimers, trimers, tetramers or other aggregates. Formation of "hot spots" for SECARS detection may be associated with particular aggregates or colloids (optionally with ionic compounds) of nanoparticles. Certain embodiments of the invention may use heterogeneous mixtures of aggregates or colloids of different size, while other embodiments may use homogenous populations of nanoparticles and/or aggregates or colloids (optionally with ionic compounds). In certain embodiments of the invention, aggregates containing a selected number of nanoparticles (e.g., dimers, trimers, etc.) may be enriched or purified by known techniques, such as ultracentrifugation in sucrose gradient solutions. In various embodiments of the invention, nanoparticle aggregates or colloids (optionally with ionic compounds) of about 5, 10, 20, 40, 60, 80, 100, 200, 300, 400, 500, 600, 700, 800, 900 to 1000 nm in size or larger are used. In particular embodiments of the invention, nanoparticle aggregates or colloids (optionally with ionic compounds) may be between about 10 nm and about 200 nm in size.

The nanoparticles may be crosslinked to form aggregates by techniques known in the art. For example, gold nanoparticles may be cross-linked, for example, using bifunctional linker compounds bearing terminal thiol or sulfhydryl groups. In some embodiments of the invention, a single linker compound may be derivatized with thiol groups at both ends. Upon reaction with gold nanoparticles, the linker would form nanoparticle dimers that are separated by the length of the linker. In other embodiments of the invention, linkers with three, four or more thiol groups may be used to simultaneously attach to multiple nanoparticles. The use of an excess of nanoparticles to linker compounds prevents formation of multiple cross-links and nanoparticle precipitation. Aggregates of silver nanoparticles may also be formed by standard synthesis methods known in the art.

In other embodiments of the invention, the nanoparticles, aggregates, or colloids (optionally with ionic compounds), may be covalently attached to a molecular sample such as an analyte. In alternative embodiments of the invention, the molecular sample may be directly attached to the nanoparticles, or may be attached to linker compounds that are covalently or non-covalently bonded to the nanoparticles aggregates.

It is contemplated that the linker compounds used to attach molecule(s) of the sample such as an analyte may be of almost any length, ranging from about 0.05, 0.1, 0.2, 0.5, 0.75, 1, 2, 3, 4, 5, 6, 7, 8, 9, 10, 11, 12, 13, 14, 15, 16, 17, 18, 19, 20, 21, 22, 23, 24, 25, 27, 30, 35, 40, 45, 50, 55, 60, 65, 60, 80, 90 to 100 nm or even greater length. Certain embodiments of the invention may use linkers of heterogeneous length.

In one embodiment of the invention disclosed in, the molecule(s) of the sample such as an analyte may be attached to nanoparticles as they travel down a channel to form molecular-nanoparticle complex. In certain embodiments of the invention, the length of time available for the cross-linking reaction to occur may be very limited. Such embodiments may utilize highly reactive cross-linking groups with rapid reaction rates, such as epoxide groups, azido groups, arylazido groups, triazine groups or diazo groups. In certain embodiments of the invention, the cross-linking groups may be photoactivated by exposure to intense light, such as a laser. For example, photoactivation of diazo or azido compounds results in the formation, respectively, of highly reactive carbene and nitrene moieties. In certain embodiments of the invention, the reactive groups may be selected so that they can only attach the nanoparticles to a sample such as an analyte, rather than cross-linking the nanoparticles to each other. The selection and preparation of reactive cross-linking groups capable of binding to a sample such as an analyte is known in the art. In alternative embodiments of the invention, components such as analytes may themselves be covalently modified, for example with a sulfhydryl group that can attach to gold nanoparticles.

In other embodiments of the invention, the nanoparticles or other Raman active surfaces may be coated with derivatized silanes, such as aminosilane, 3-glycidoxypropyltrimethoxysilane (GOP) or aminopropyltrimethoxysilane (APTS). The reactive groups at the ends of the silanes may be used to form cross-linked aggregates of nanoparticles. It is contemplated that the linker compounds used may be of almost any length, ranging from about 0.05, 0.1, 0.2, 0.5, 0.75, 1, 2, 3, 4, 5, 6, 7, 8, 9, 10, 11, 12, 13, 14, 15, 16, 17, 18, 19, 20, 21, 21, 22, 23, 24, 25, 27, 30, 35, 40, 45, 50, 55, 60, 65, 70, 80, 90, to 100 nm or even greater length. Certain embodiments of the invention may use linkers of heterogeneous length. Such modified silanes may also be covalently attached to components such as analytes using standard methods.

In another alternative embodiment of the invention, the nanoparticles may be modified to contain various reactive groups before they are attached to linker compounds. Modified nanoparticles are commercially available, such as the Nanogold® nanoparticles from Nanoprobes, Inc. (Yaphank, N.Y.). Nanogold® nanoparticles may be obtained with either single or multiple maleimide, amine or other groups attached per nanoparticle. The Nanogold® nanoparticles are also available in either positively or negatively charged form to facilitate manipulation of nanoparticles in an electric field. Such modified nanoparticles may be attached to a variety of known linker compounds to provide dimers, trimers or other aggregates of nanoparticles.

The type of linker compound used is not limiting. In some embodiments of the invention, the linker group may comprise phenylacetylene polymers. Alternatively, linker groups may comprise polytetrafluoroethylene, polyvinyl pyrrolidone, polystyrene, polypropylene, polyacrylamide, polyethylene or other known polymers. The linker compounds of use are not limited to polymers, but may also include other types of molecules such as silanes, alkanes, derivatized silanes or derivatized alkanes. In particular embodiments of the invention, linker compounds of relatively simple chemical structure, such as alkanes or silanes, may be used to avoid interfering with the Raman signals emitted by a sample such as an analyte.

Alternatively, the linker compounds used may contain a single reactive group, such as a thiol group. Nanoparticles containing a single attached linker compound may self-aggregate into dimers, for example, by non-covalent interaction of linker compounds attached to two different nanoparticles. For example, the linker compounds may comprise alkane thiols. Following attachment of the thiol group to gold nanoparticles, the alkane groups will tend to associate by hydrophobic interaction. In other alternative embodiments of the invention, the linker compounds may contain different functional groups at either end. For example, a liker compound could contain a sulfydryl group at one end to allow attachment to gold nanoparticles, and a different reactive group at the other end to allow attachment to other linker compounds. Many such reactive groups are known in the art and may be used in the present methods and apparatus.

In other embodiments of the invention, a sample such as an analyte is closely associated with the surface of the nanoparticles or may be otherwise in close proximity to the nanoparticles (between about 0.2 and 1.0 nm). As used herein, the term "closely associated with" refers to a molecular sample such as an analyte which is attached (either covalent or non-covalent) or adsorbed on a Raman-active surface. The skilled artisan will realize that covalent attachment of a molecular sample such as an analyte to nanoparticles is not required in order to generate a surface-enhanced Raman signal by SECARS.

(b) Metal Coated- and Non-Metal Coated Nanocrystalline and/or Porous Silicon

In some embodiments of the invention, the Raman active surface could be provided by metal coated- and non-metal coated nanocrystalline and/or porous silicon. Methods for producing nanocrystalline silicon include, but are not limited to, silicon (Si) implantation into a silicon rich oxide and annealing; solid phase crystallization with metal nucleation catalysts; chemical vapor deposition; PECVD (plasma enhanced chemical vapor deposition); gas evaporation; gas phase pyrolysis; gas phase photopyrolysis; electrochemical etching; plasma decomposition of silanes and polysilanes; high pressure liquid phase reduction-oxidation reactions; rapid annealing of amorphous silicon layers; depositing an amorphous silicon layer using LPCVD (low pressure chemical vapor deposition) followed by RTA (rapid thermal anneal) cycles; plasma electric arc deposition using a silicon anode and laser ablation of silicon. Depending on the process, Si crystals of anywhere from 1 to 100 nm or more in size may be formed as a thin layer on a chip, a separate layer and/or as aggregated crystals. In certain embodiments of the invention, a thin layer comprising nanocrystalline silicon attached to a substrate layer may be used.

In certain embodiments of the invention, the size and/or shape of silicon crystals and/or pore size in porous silicon may be selected to be within predetermined limits, for example, in order to optimize the plasmon resonant frequency of metal-coated porous silicon. The plasmon resonant frequency may also be adjusted by controlling the thickness of the metal layer coating the porous silicon and/or the size of nano-scale silicon crystals are known.

In certain embodiments of the invention, a molecular sample such as an analyte could be moved down a flow path or channel, such as a microfluidic channel, nanochannel, or microchannel and/or a sample stage, and past a detection unit of the apparatus. In accordance with such embodiments, the Raman-active surfaces and components such as analytes may be incorporated into a larger apparatus and/or system. In certain embodiments, the Raman-active surfaces may be incorporated into a micro-electro-mechanical system (MEMS). The sensor components of MEMS may be used to measure mechanical, thermal, biological, chemical, optical and/or magnetic phenomena. The electronics may process the information from the sensors and control actuator components such pumps, valves, heaters, coolers, filters, etc. thereby controlling the function of the MEMS.

In certain embodiments of the invention, the metal coated silicon layer may be incorporated as an integral part the sample stage. In alternative embodiments, the metal-coated silicon may be cut out of a silicon wafer and incorporated into a chip and/or other device.

In some embodiments of the invention, the Raman active surface may be connected to various fluid filled compartments, such as microfluidic channels, nanochannels and/or microchannels. These and other components of the apparatus may be formed as a single unit, for example in the form of a chip as known in semiconductor chips and/or microcapillary or microfluidic chips. Alternatively, the Raman active surface may be removed from a silicon wafer and attached to other components of an apparatus. Any materials known for use in such chips may be used in the disclosed apparatus, including silicon, silicon dioxide, silicon nitride, polydimethyl siloxane (PDMS), polymethylmethacrylate (PMMA), plastic, glass, quartz, etc. In certain embodiments of the invention, it is contemplated that the microfluidic channel will have a diameter between about 3 nm and about 1 micron. In particular embodiments of the invention, the diameter of the microfluidic channel may be selected to be slightly smaller in size than an excitatory laser beam. Techniques for batch fabrication of chips are well known in the fields of computer chip manufacture and/or microcapillary chip manufacture. Such chips may be manufactured by any method known in the art, such as by photolithography and etching, laser ablation, injection molding, casting, molecular beam epitaxy, dip-pen nanolithography, CVD fabrication, electron beam or focused ion beam technology or imprinting techniques. Non-limiting examples include conventional molding with a flowable, optically clear material such as plastic or glass; photolithography and dry etching of silicon dioxide; electron beam lithography using polymethylmethacrylate resist to pattern an aluminum mask on a silicon dioxide substrate, followed by reactive ion etching; Methods for manufacture of nanoelectromechanical systems may be used for certain embodiments of the invention. Various forms of microfabricated chips are commercially available from sources such as Caliper Technologies Inc. (Mountain View, Calif.) and ACLARA BioSciences Inc. (Mountain View, Calif.).

For fluid-filled compartments that may be exposed to various single biomolecules, such as proteins, peptides, nucleic acids, nucleotides and the like, the surfaces exposed to such molecules may be modified by coating, for example to transform a surface from a hydrophobic to a hydrophilic surface and/or to decrease adsorption of molecules to a surface. Surface modification of common chip materials such as glass, silicon, quartz and/or PDMS are possible contemplated as embodiments of the invention. Such modifications may include, but are not limited to, coating with commercially available capillary coatings (Supelco, Bellafonte, Pa.), silanes with various functional groups such as polyethyleneoxide or acrylamide, or any other coating known in the art.

To facilitate detection of a sample such as an analyte, one embodiment of the invention comprises materials that are transparent to electromagnetic radiation at the excitation and emission frequencies used. Glass, silicon, quartz, or any other materials that are generally transparent in the frequency ranges used for Raman spectroscopy may be used. Any geometry, shape, and size is possible for the sample stage since any refraction which this component introduces can be ignored or compensated for.

In some embodiments of the invention, use of charged linker compounds or charged nanoparticles may facilitate manipulation of nanoparticles through the use of electrical gradients. In other embodiments of the invention, the sample stage and/or flow path may contain aqueous solutions with relatively high viscosity, such as glycerol solutions. Such high viscosity solutions may serve to decrease the flow rate and increase the reaction time available, for example, for cross-linking components such as analytes to nanoparticles. In other embodiments of the invention, sample stages and/or flow paths may contain nonaqueous solutions, including, but not limited to organic solvents.

The sample to be analyzed and the metallic particulate or colloidal surfaces can be delivered to the sample stage by various means. For example, the metallic particulate or colloidal surfaces can be delivered to the sample of molecule(s) to be analyzed, the sample of molecule(s) to be analyzed can be delivered to metallic particulate or colloidal surfaces, or the molecule(s) to be analyzed and metallic particulate or colloidal surfaces may be delivered simultaneously. If the sample is in liquid form, the sample to be analyzed and/or metallic particulate or colloidal surfaces can be delivered automatically by a device which pumps or otherwise allows the sample to flow into the sample stage. Such a device includes linear microfluidic devices. In another embodiment, the sample to be analyzed and/or the metallic particulate or colloidal surfaces can be placed directly into the sample stage.

Several different embodiments include, but are not limited to the use of, various wavelengths, waveguides, optical couplings/choice of pump beams, and the like in order to achieve a precise emission orientation that allows for the detection and identification of a sample of only a small number of molecules of a sample such as an analyte. For example, the two separate wavelengths of Raman light may be chosen to correspond to the vibrational energy level of the target analyte and to orient the highly directional output. For example, in order to probe adenine ring breathing mode at 735 $cm^{-1}$, the excitation light can be tuned to 785 nm and the Stokes light can be tuned to 833 nm so that their energy level difference matches the vibrational energy level of 735 $cm^{-1}$.

Raman Labels

Certain embodiments of the invention may involve attaching a label to one or more molecules of a sample such as an analyte to facilitate their measurement by the Raman detection unit. Non-limiting examples of labels that could be used for Raman spectroscopy include TRIT (tetramethyl rhodamine isothiol), NBD (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxytetramethyl amino phthalocyanines, azomethines, cyanines, xanthines, succinylfluoresceins, aminoacridine, quantum dots, carbon nanotubes, fullerenes, organocyamides, such as isocyamide, and the like.

Polycyclic aromatic compounds may function as Raman labels, as is known in the art. Other labels that may be of use for particular embodiments of the invention include cyamide, thiol, chlorine, bromine, methyl, phosphorus and sulfur. In certain embodiments of the invention, carbon nanotubes may be of use as Raman labels. The Raman labels used should generate distinguishable Raman spectra and may be specifically bound to or associated with different types of samples such as analytes.

Labels may be attached directly to the molecule(s) of a sample such as an analyte or may be attached via various linker compounds. Cross-linking reagents and linker compounds of use in the disclosed methods are further described below.

Some of the embodiments of U.S. application Ser. Nos. 10/688,680 and 10/966,893 permit a user to put a liquid sample dispersed in a solution in the sample stage and to collect the Raman spectrum of the sample as a whole dispersed in the solution. The embodiments the invention permit a user to put a solid or liquid sample in the sample stage and systematically move the sample stage or steer the beam across the body of the sample to collect information from different parts of the sample.

One embodiment of the invention is to utilize a motorized stage to collect data from different locations of the sample. Placing a sample on a motorized stage enables collection of the SECARS signal from a specific location inside the sample, and the information can be used to construct a 2D or 3D image of the sample. Initially, the sample could be positioned so that the SECARS signal can be collected. Then if this is not the last position, the stage moves, typically by 1 micron in one direction. The SECARS signal is collected again. This is repeated to form a raster scanning pattern in 2D or 3D until the last point of interest has been scanned. The SECARS signal intensity collected can be used to reconstruct the 2D or 3D image of the sample, similar to the method known in two photon microscopy or confocal microscopy.

In an alternative embodiment, the laser beams can be reflected by a scanning mirror set, which might comprise of a single mirror mounted on a dual axis scanner, or of two mirrors, each of which is mounted on a single axis scanner where the movement direction of the scanners are aligned perpendicularly. Optionally, a mechanical movement in the third axis could be used to obtain three-dimensional data.

Applications of the Embodiments of the Invention

The applications of the embodiment of this invention include material inspection, biologic cell or tissue imaging, and in vivo imaging, particularly of a sample obtained from a biological source. The sample could be a biological cell or tissue. For example, the sample could be a phosphorylated peptide. In this case, by the embodiments of this invention, the user can detect the position and spatial location of phosphorylation within the sample by either systematically moving the sample stage or steering the beam through the body of the sample. Also, by the embodiments of this invention, the user can do imaging of multiple layers of tissues, for example.

Typically, a sample obtained from a biologic source, such as for example, a bodily fluid or cell lysate solution, is a complex mixture of proteins and other molecules. The components of the mixture can be separated using known techniques for isolating protein fractions from biologic samples, such as for example, physical or affinity based separation techniques. The isolated proteinaceous fraction can then be digested into smaller peptides. Typical methods include enzymatic digestions such as for example, proteinase enzymes such as, Arg-C(N-acetyl-gamma-glutamyl-phosphate reductase), Asp-N, Glu-C, Lys-C, chromotrypsin, clostripain, trypsin, and thermolysin. The resulting digest of peptides can be further separated, for example, using HPLC (high pressure liquid chromatography). Raman spectroscopy can then be performed on the resulting sample by, for example, mixing the digested sample with a SERS solution, such as for example, a colloidal silver solution, depositing and drying the digested sample onto a substrate and subsequently adding a SERS solution, such as a colloidal silver solution, depositing the sample onto a SERS-active substrate, or it can be performed in-line in a component of a microfluidic or nanofluidic system, such as by using a micro or nanomixer to mix the SERS solution with a the digested sample and subsequently performing Raman analysis on the sample. A silver colloidal solution can be mixed with digested sample eluants in a fluidic format (optionally, on a chip) and the detection can be performed inline as the eluants are flowing through the laser detection volume. In additional embodiments, some or all of these steps are performed using microfluidics.

Figure 10:
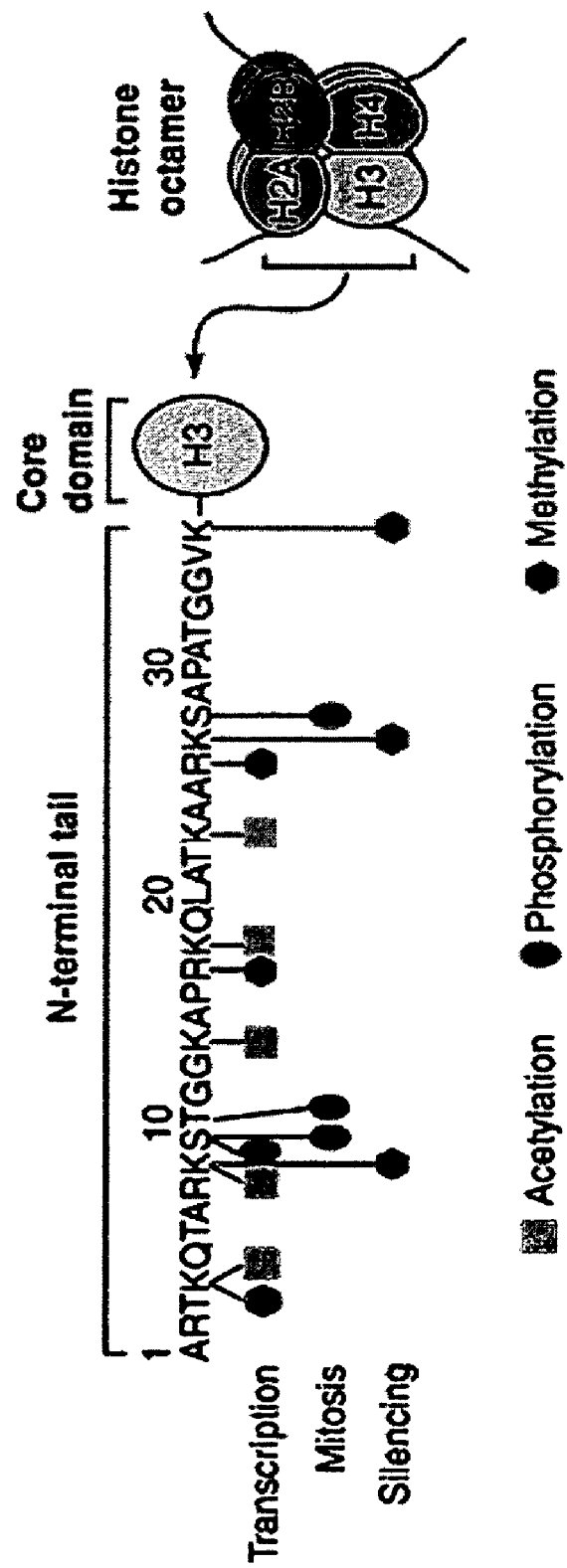
FIG. 10 shows the structure of the N-terminal tail of Histone H3 and indicates the biological significance of illustrated post translational modifications.

In additional embodiments, the present invention provides the ability to detect the presence of post-translational modifications of similar mass on peptides using SERS. For example, part of the N-terminal tail of histone H3 ($^9$KSTG-GKAPR) (P) has lysines at the amino-acid positions 9 and 14 that are frequently targeted for modifications such as acetylation and methylation. Similarly, the serine and threonine at amino acid positions 10 and 11 in this peptide, P, are targeted for phosphorylation. (See FIG. 10 for a map of biologically significant modification sites.) These modifications are known to have major effects on the histone-histone as well as the histone-regulatory protein interactions.

In material inspection, either the material of interest is preferably made of metal or goes through a coating process so that the material is coated with metal to facilitate the use of SECARS. Then, the material is scanned by the CARS instrument to obtain chemical composition information in 2D or 3D. Alternatively, the surface can be further coated with signal generating molecules (e.g. typically dye molecules such as rhodamine 6G) and scanned to obtain the sub-micron topography of the material in 2D or 3D.

For biological imaging of cells or tissue by the embodiments of this invention, the cell or tissue to be analyzed could be stained with metallic nanoparticles. The metallic nanoparticles may settle on the cell or tissue surface, or may bind to specific molecules in the cell or tissue, if the nanoparticles are coated with antibodies. Alternatively, the nanoparticles may contain signaling molecules (e.g. composite organic-inorganic nanoparticles (COIN) or other SERS labels). Again, the biological medium (cell or tissue) stained with the metallic nanoparticles is scanned by the CARS instrument to obtain chemical composition information or topography in 2D or 3D.

In in vivo imaging, nanoparticles are injected into the animal or human, as is used to enhance the magnetic resonance imaging (MRI) data. By scanning the animal or human using the CARS instrument, the chemical composition and distribution inside the body could be detected.

Figure 11:
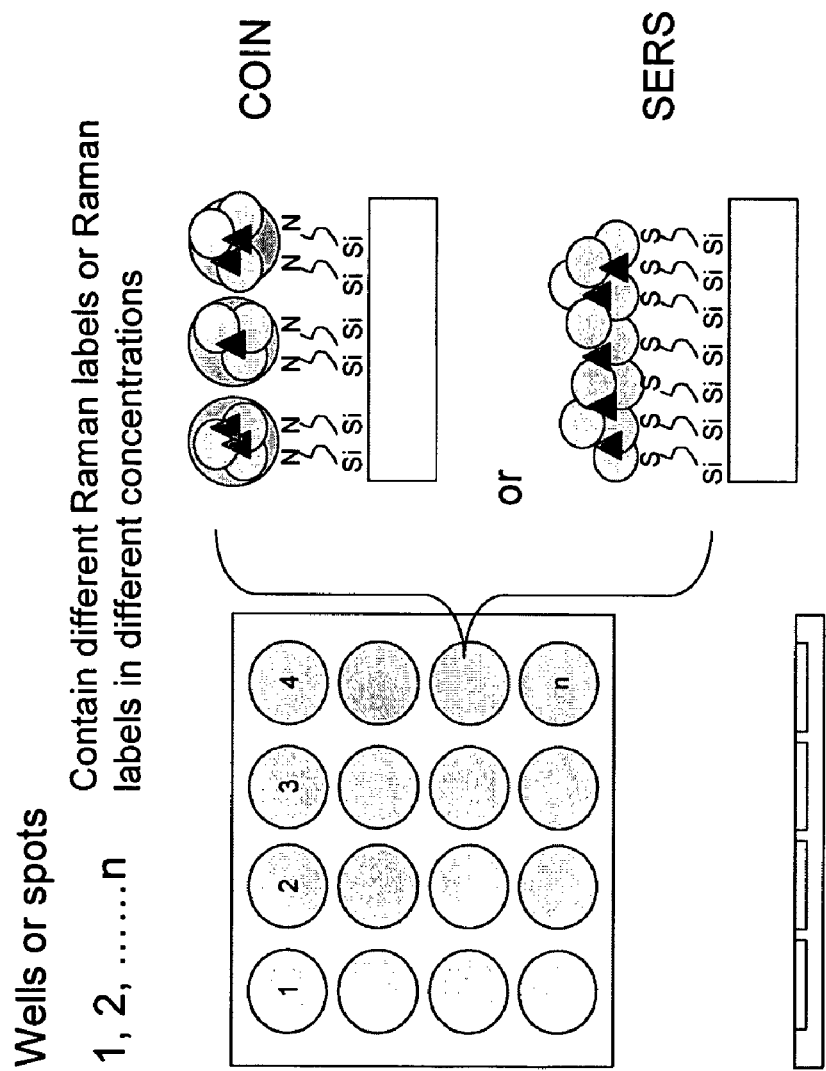
FIG. 11 shows an array of SERS active particles.

The sample could also be an array comprising SERS active particles such as that shown in FIG. 11. The array includes a plurality of spots attached to a substrate. Each of the spots may be the same or may include a different composition and/or concentration of SERS active particles. The array can be a multiple-well array or a surface containing multiple sub-surfaces.

For a sub-surface array, a sample such as an analyte is exposed to various SERS sites or COINs formed with different Raman labels, with which the analyte interacts differently. Thus the signal patterns (spectral shapes or intensities) are used for analyte identification. A Raman spectrometer and related software are part of the detection system.

In one embodiment, the SERS active particles could be COIN particles. The COIN particles may include Raman-active compounds. Each spot on the array may include the same COIN particles. Alternatively, each spot in the array may include different COIN particles. For example each spot may employ COINs having Raman active compounds having different structures, mixtures, and concentrations.

The array of COIN particles can be used to identify both Raman active and non Raman active analytes. Non Raman active compounds can be identified using the COIN array because these compounds can interact with one or more of the COINs in the array or otherwise alter the COIN signatures. Since different compounds may interact with different COIN particles, by having different spots contain different COIN particles, a sample containing an analyte can be tested for its interaction with several different COIN particles simultaneously.

The COIN array can be made, for example, by contact printing methods as used for DNA or protein microarray fabrication since COIN particles are nano size dimension and thus remain in solution in colloidal state. In addition, COIN arrays may also be made by non-contact printing methods, similar to inject printing method, where print heads are filled with different COIN solutions. After delivering COIN particles onto a solid support substrate, COIN particles can be immobilized by chemical cross-linking through functional groups on the COIN surface and the substrate surface. The COIN particles can also be attached to the substrate utilizing bi-functional linkers.

In another embodiment the SERS array could include surface enhanced Raman scattering active particles that do not contain Raman-labels. For example, gold silver, platinum copper or aluminum particles can be placed in the array to enhance the Raman spectra of Raman active analytes. Silver colloidal particles have been found to be particularly useful for SERS arrays. Since these SERS active particles do not themselves produce the detected Raman spectra, the sample such as an analyte must produce a detectable Raman Spectra. However, surface enhanced Raman scattering (SERS) techniques make it possible to obtain many-fold Raman signal enhancement, for example, by about 10 to about 10000 fold increase, more preferably, about 100 to about 1000 fold increase. Such huge enhancement factors could be attributed primarily to enhanced electromagnetic fields on curved surfaces of coinage metals. Although the electromagnetic enhancement (EME) has been shown to be related to the roughness of metal surfaces or particle size when individual metal colloids are used, SERS is most effectively detected from aggregated colloids. For example, chemical enhancement can also be obtained by placing molecules in a close proximity to the surface in certain orientations.

EXAMPLES

Manufacture of the improved SECARS equipment (1) Embodiment of FIG. 3

FIG. 3 is a schematic diagram of an experimental setup of a preferred embodiment. Two picoseconds Ti:sapphire lasers, each generating 3 picoseconds pulses at 76 MHz repetition rate, are synchronized by a phase-locking device. The polarization of the Stokes laser is modulated by a half-waveplate. Two laser pulses are overlapped by a dichroic mirror DM1. The overlapped beam is focused onto a sample by a microscope objective. The back-scattered SECARS signal is collected by the same objective, and both laser lines are blocked by a bandpass filter. The filtered light is sent to a spectrometer, where the dispersion of light is recorded by a liquid nitrogen cooled CCD camera. The temporal overlap of laser pulses is monitored by the autocorrelator. In FIG. 3, the abbreviations are as follows: LF, laser line filter; HW, half-waveplate; DM, dichroic mirror; BF, bandpass filter; P, polarizer; MO, microscope objective; S, sample.

Details of manufacturing the improved SECARS equipment are as follows. The CARS setup is configured in a collinear excitation-collection geometry. The tight focusing of the microscope objective relaxes the phase-matching condition and allows SECARS measurements without adjustment of the incident angle of the excitation beams for probing multiple vibrational bands. The steps to manufacture an embodiment of the improved SECARS equipment is as follows:

1. Place two picoseconds titanium-doped sapphire lasers (e.g. Mira laser manufactured by Coherent, Santa Clara, Calif.), each of which is powered by a green laser, such as an argon-ion laser (e.g. Innova laser manufactured by Coherent) or a solid-state laser (e.g. Verdi laser manufactured by Coherent). One of the lasers will operate at a fixed wavelength during the measurement. The wavelength of the other laser can be tuned depending on the molecule to be detected. We call the laser with the fixed wavelength a "pump" laser and the other laser a "Stokes" laser.
2. Place beam samplers in front of the lasers. The beam sampler transmits 95-99% of the incident light, and reflects the rest of light. The reflected beams are focused into optical fibers which are connected to a phase-lock (e.g. SynchroLock AP manufactured by Coherent, Santa Clara, Calif.). The phase-lock compares the laser pulses generated by the two lasers and automatically adjusts the phase of one of the two titanium-doped sapphire lasers so that the laser pulses from the two lasers have a constant phase delay.

3. Optionally, place beam isolators after the beam samplers to prevent the laser beam reflected by other optical components from re-entering the lasers. Otherwise, a severe reflection can interfere with the stable operation of the lasers.

4. Optionally, place a laser line filter after the beam sampler for the pump laser. The laser line filter is designed to transmit primarily the laser wavelength and block any other background light generated by the laser.

5. Place a half-wave plate after the beam sampler for the Stokes laser. The half-wave plate should be mounted in a rotational stage so that its angle along the optical axis can be adjusted.

6. Place a mirror and a dichroic mirror ("DM1") to spatially overlap the two laser beams. The two laser beams should propagate coaxially after the dichroic mirror. The dichroic mirror is designed to either 1) reflect the pump laser beam and transmit the Stokes laser beam, or 2) reflect the Stokes laser beam and transmit the pump laser beam.

7. Place a dichoric mirror ("DM2") to steer the spatially overlapped laser beam toward the sample.

8. Place a beam sampler to reflect the spatially overlapped laser beam toward the auto-correlator. The auto-correlator compares the laser pulses and displays the phase delay between the pulses.

9. Place a microscope objective to focus the laser beam transmitted through the beam sample onto the sample.

10. Place an XYZ stage that can move the sample in X, Y, and Z directions with 1 micron resolution or better.

11. Once the sample is positioned on the XYZ stage, and if the lasers are operating, the sample generates an optical signal, which is collected by the microscope objective and transmitted toward the dichroic mirror DM2. Place a bandpass filter along the optical pathway. The bandpass filter blocks the laser wavelengths and transmits primarily the optical signal from the sample.

12. Place a polarizer after the beam sampler for the Stokes laser. The polarizer should be mounted in a rotational stage so that its angle along the optical axis can be adjusted.

13. Place a spectrograph mounted with a CCD camera to analyze the optical signal.

14. Optionally, place a lens between the polarizer and the spectrograph to focus the beam of optical signal onto the entrance plane of the spectrograph.

Figure 13:
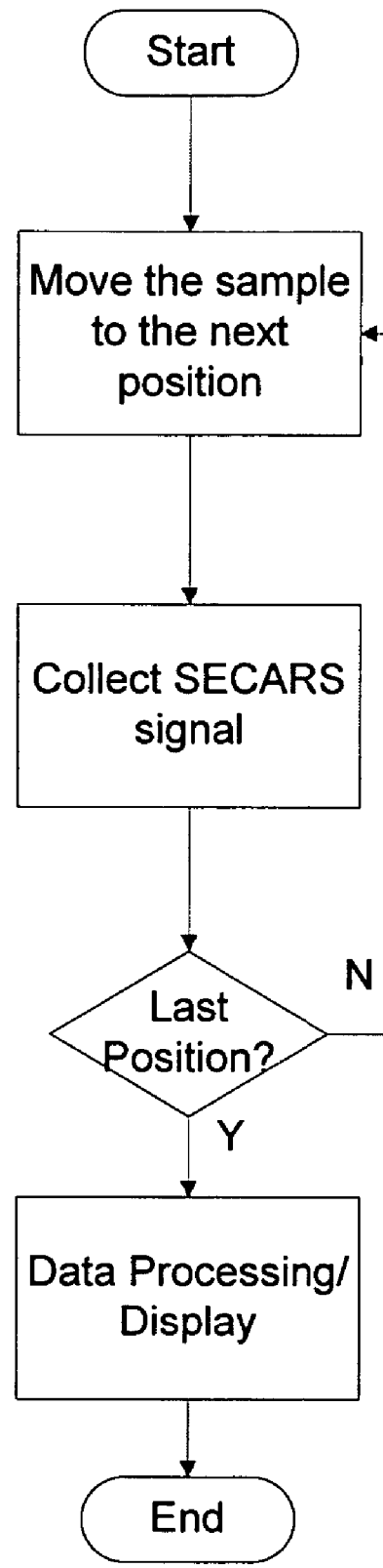
FIG. 13 shows the algorithm for processing the data generated by the devices of the embodiments of the invention.

15. Connect the CCD and the stage to a microprocessor and install a software that will operate the CCD camera, control the stage movements, and process the data (explained below with reference to FIG. 13).

16. Mirrors can be used as necessary to change the direction of beams and optical signal as long as they do not interfere with the overall operation of the equipment. Dielectric mirrors are preferred but any other reflective surface that does not interfere with the overall operation of the equipment can be used.

(2) Alternative Embodiments

The following alternative embodiments are also possible.
1. Alternative Light Source (a) Alternative embodiment 1A (FIG. 4)

Instead of using a second titanium-doped sapphire laser and a phase lock, an optical parametric oscillator (OPO) can be used to generate the second laser beam. OPO takes a laser beam of one wavelength and generates a laser beam of another wavelength (FIG. 4). In this configuration, the beam sampler in the step 2 above should be replaced with a surface with higher reflection (20-80%).

(b) Alternative Embodiment 1B (FIG. 5)

OPO generates two laser beams, and in another alternative embodiment, the two laser beams generated by OPO can be used instead of laser beams generated by two titanium-doped sapphire lasers (FIG. 5). In this configuration, the beam from the titanium-doped sapphire laser is directed toward OPO and two laser beams generated by OPO are used.

2. Alternative Scanning Method (FIG. 6)

Instead of using the positioning stage, a scanning mirror can be used instead for illuminating and collecting optical signal from different location on the sample (FIG. 6). In this configuration, the stage could move in the Z direction during scanning or the combination of the scanning mirror and the microscope objective could move in the Z direction, while scanning in the X and Y directions could be performed by the scanning mirror.

3. Alternative Detectors (a) Photodiode (PD) with no Spectrometer (FIG. 7)

For a faster detection, an alternative detector can be utilized. In place of the dispersive spectrograph and the CCD camera, a single channel detector or a low-density detector can be used (FIG. 7) to detect the intensity of different Raman peaks of the Raman spectra emitted by the sample, but not the frequency of the different Raman peaks as the detector does not include a spectrometer. Such detectors include a photodiode, a photomultiplier tube, or an avalanche photodiode.

(b) Photodiode with a Non-Dispersive Spectrometer (FIG. 8)

In place of a dispersive spectrograph, a non-dispersive spectrograph can be used. FIG. 8 shows a configuration where a Fourier-transform spectrometer is used. The use of a Fourier-transform spectrometer allows, but not limited to, the use of a single channel detector, such as a photodiode, a photomultiplier tube, or an avalanche photodiode. A single channel detector is typically less expensive than a multi-channel detector, such as a CCD camera.

Figure 12:
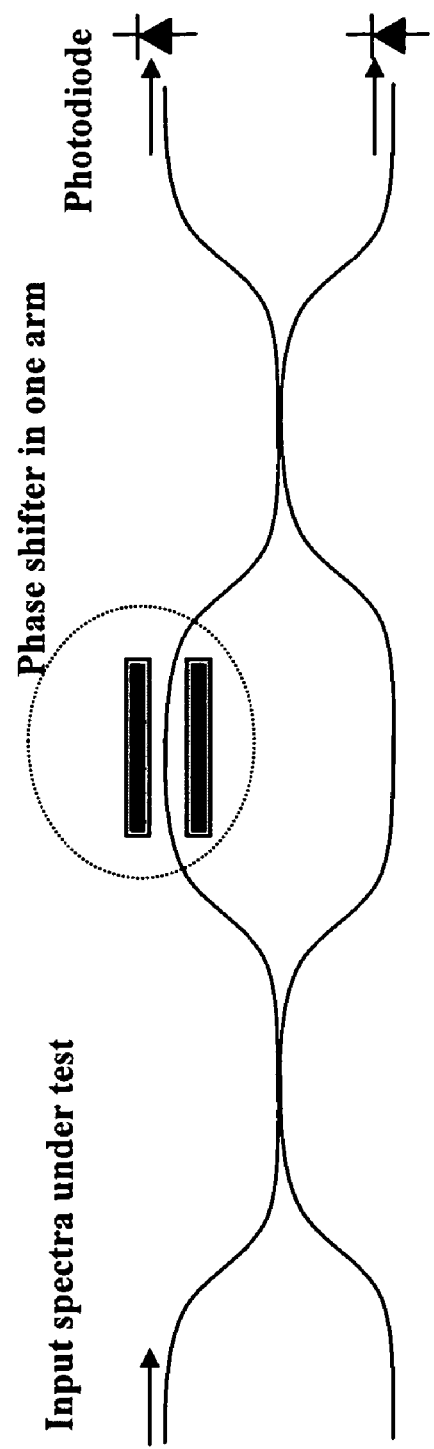
FIG. 12 shows an embodiment of a Fourier transform non-dispersive spectrometer in combination with a photodiode.

FIG. 12 shows an embodiment of a Fourier transform non-dispersive spectrometer in combination with a photodiode, which is functionally similar to the Michelson interferometer. However, instead of creating the phase delay by changing the path length difference as in the Michelson interferometer, in the Fourier transform non-dispersive spectrometer a variable index-of-refraction material could be put into one of the two beam paths. By carefully controlling the index-of-refraction of the material, different interference fringes could be formed, which can be recorded by a single channel detector such as a photodiode, for example, as an Fourier transform spectrum. Subsequently, the Fourier transform spectrum could be inverse Fourier transformed by a microprocessor to obtain the Raman spectrum of the sample such as an analyte. The Fourier transform non-dispersive spectrometer in combination with a photodiode would not require a spectrometer having a dispersive grating or having any moving parts.

4. Single Laser Beam Embodiment (FIG. 9)

Figure 9:
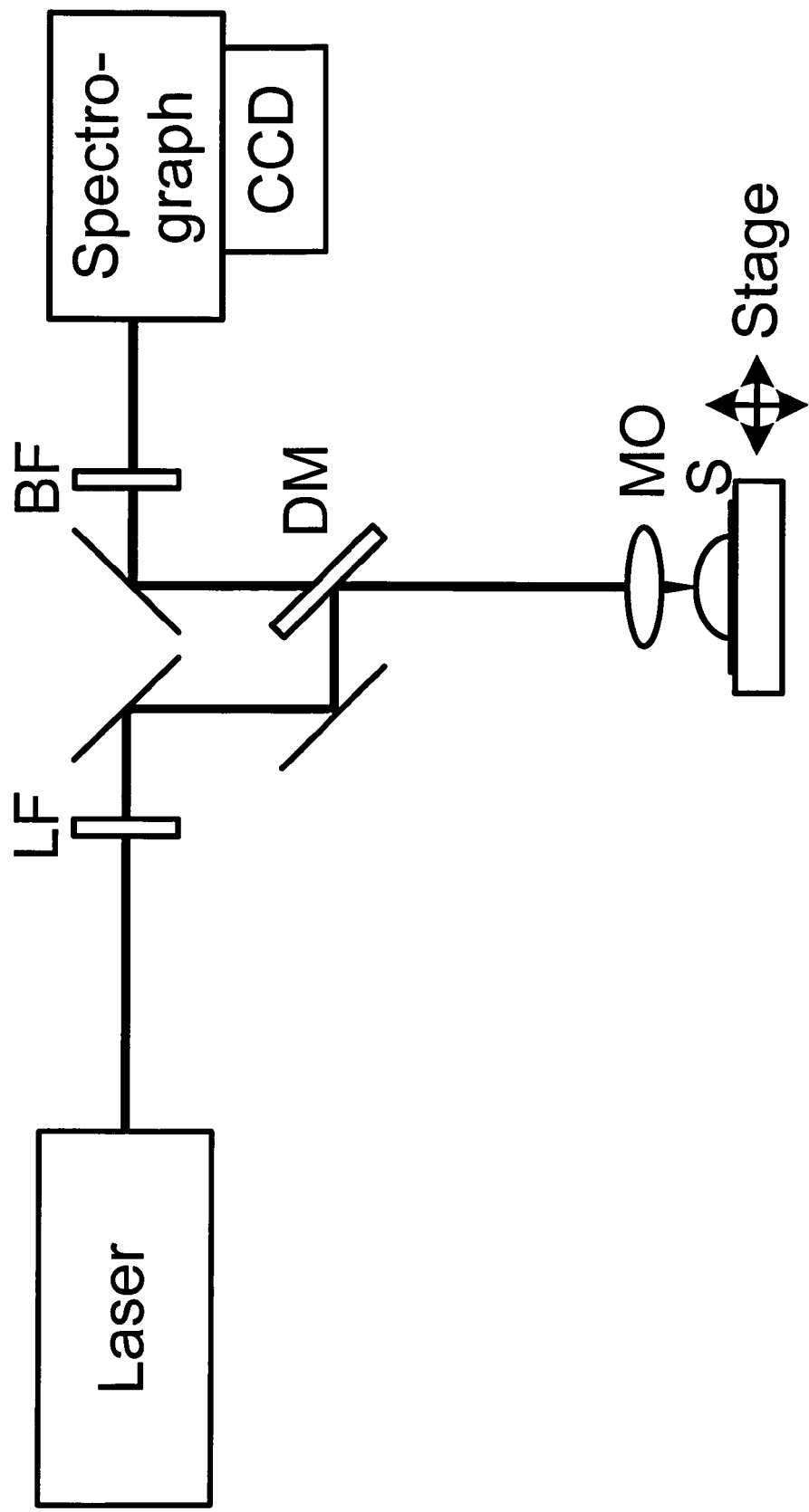
FIG. 9 shows an embodiment of an improved SERS device of this invention.

Schematic diagram of the single laser SERS imaging setup is shown in FIG. 9. A single laser generates a laser beam. The laser beam is focused onto a sample by a microscope objective. The back-scattered signal is collected by the same objective, and the laser line is blocked by a bandpass filter. The filtered light is sent to a spectrometer, where the dispersion of light is recorded by a liquid nitrogen cooled CCD camera.

Details of a Step-by-Step Method of Using the Improved SECARS Equipment

The steps to use the improved SECARS equipment are as follows:
1. Turn on the lasers and the phase-lock.
2. Monitor wavelength of each laser using a wavelength-meter or a spectrometer, and tune the Stokes laser so that its wavelength matches $\lambda_{Stokes}$ calculated by the following equation:

$$w=10^7/\lambda_{pump}-10^7/\lambda_{Stokes},$$

where w is the wavenumber of the known vibrational band of the molecule to be detected (in $cm^{-1}$ unit), and $\lambda_{pump}$ and $\lambda_{Stokes}$ are the wavelengths of the pump and Stokes laser beams (in nanometer unit). Utilizing the equation above, $\lambda_{Stokes}$ can be calculated with the wavenumber of the known vibration band and $\lambda_{pump}$.
3. Monitor the pulse width of the laser beams with an auto-correlator and ensure that each laser operates in the picoseconds pulsed mode.
4. Engage the phase-lock so that the phase delay between the two laser beams is constant.
5. Monitor the phase delay of the two laser beams near the microscope objective using the auto-correlator, and adjust the phase delay in the phase-lock so that the laser pulses from the two lasers temporarily overlap upon reaching the sample.
6. Adjust the angle of the half-wave plate and the polarizer to minimize the background signal.
7. Prepare the sample. The sample can be prepared in many different ways including the following:
   a. In one method, the sample is placed on a SERS active substrate. The method to fabricate the SERS active substrate is known in the field (S. Chan, S. Kwon, T.-W. Koo, L. P. Lee, and A. A. Berlin, Adv. Mater. 15, 1595 (2003)) and has been explained above.
   b. In another method, the sample is treated with SERS active nanoparticles. SERS active nanoparticles can be commercially purchased (e.g. gold nanoparticles manufactured by Ted Pella) or can be manufactured by methods well known in the field (e.g. P. C. Lee and D. Meisel, "Adsorption and surface-enhanced Raman of dyes on silver and gold sols," J. Phys. Chem. 86, 3391-3395 (1982)). The nanoparticle solution is directly sprayed upon the sample or the nanoparticles can be conjugated with specific binding moiety, such as antibodies, to bind to specific target molecules in the sample. Optionally, add the chemical enhancer to the sample-colloid mixture. The chemical enhancer can be sodium chloride, lithium chloride, or other ionic salts as is known in the field (e.g. T. Koo, S. Chan, L. Sun, X. Su, J. Zhang, and A. A. Berlin, Appl. Spectrosc. 58, 1401 (2004)).
   c. In yet another method, mix the sample with the nanoparticle solution, and add the chemical enhancer to the mixture. The nanoparticles can be conjugated with specific binding moiety or can be used without conjugation.
8. Place the mixture on the stage.
9. Operate the software which automatically collects the data and move the sample to the next location Application of the improved SECARS device In the past, mass spectrometry (MS) has been a favored approach for proteome-wide post-translational modification (PTM) profiling due to its sensitivity for measuring and locating molecular weight changes in proteins and peptides. However, some modifications such as acetylation and trimethylation of lysine (both have nominal mass increases of 42 Da) and phosphorylation and sulfation of tyrosine (both have a nominal mass increases of 80 Da) require expensive, high-resolution mass spectrometers or require mass spectrometry analysis schemes that are not conducive to high-throughput analyses. Also, modifications such as phosphorylation, sulfation, and glycosylation are unstable during tandem mass spectrometry experiments making identification and positional information difficult to obtain. In few cases, quantification of protein expression and modifications using mass spectrometry has been performed using stable isotope labeling techniques.

Figure 14:
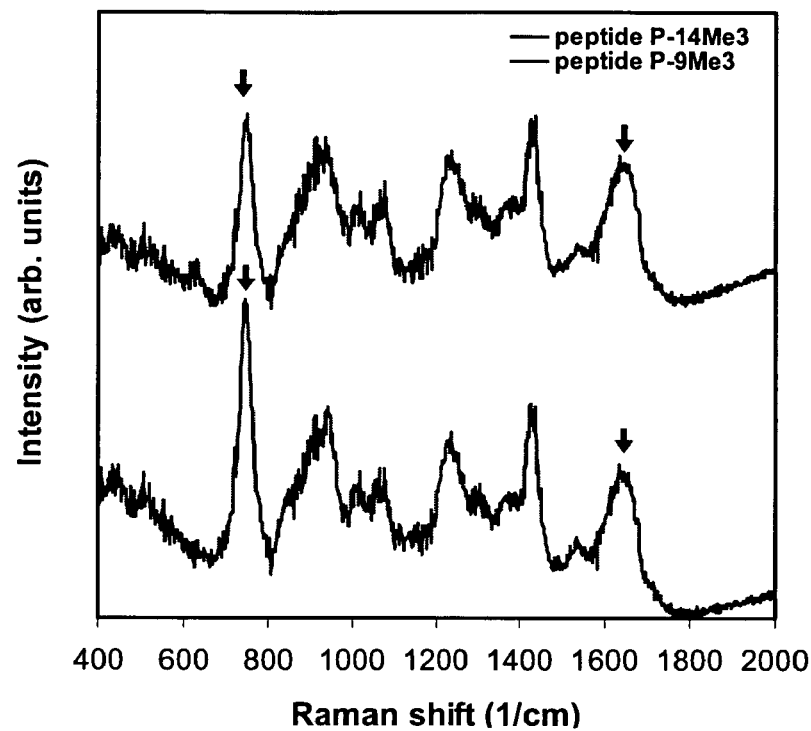
FIG. 14A and FIG. 14B illustrate the positional dependence in SERS spectra for two different protein modification: trimethylation and phosphorylation.
Figure 14:
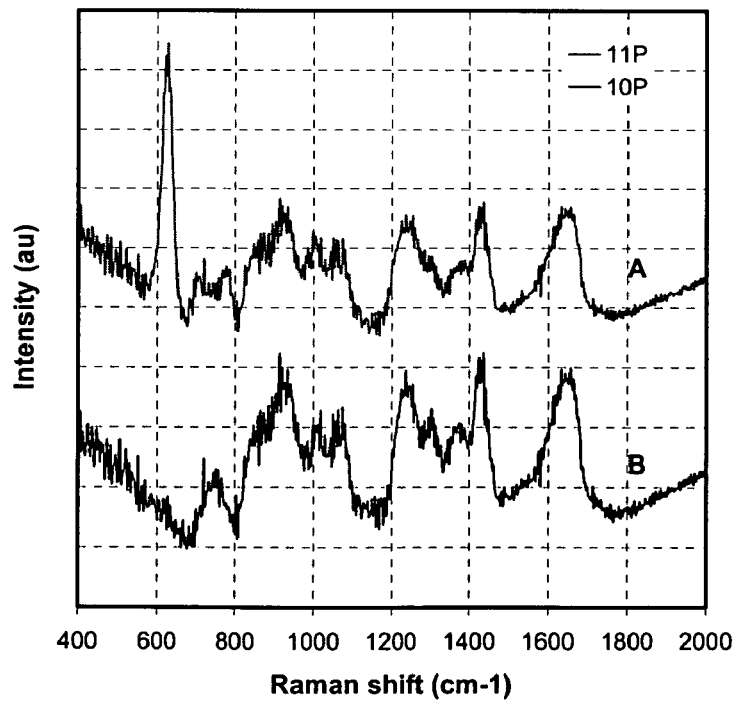

However, in further embodiments of this invention, SERS and SECARS could be used for detection and analysis of labile post translational modifications, such as, for example, phosphorylation. FIG. 14A and FIG. 14B illustrate positional dependence in SERS spectra for two different protein modifications: trimethylation and phosphorylation. In FIG. 14A, the upper line illustrates the SERS spectrum of a peptide that has been trimethylated at a lysine located in the middle of the peptide chain ($^9$KSTGG$^{14}$K(trimethylated)APR) (P-14Me3), and the bottom line illustrates the SERS spectrum of a peptide having the same sequence that has been trimethylated at the lysine located at the N-terminus of the peptide ($^9$K(trimethylated)STGGKAPR) (P-9Me3). Spectra were taken at concentrations of 9 ng/μL and arbitrarily offset along the y-axis. In FIG. 14B, the upper line illustrates the SERS spectrum of a peptide that has been phosphorylated at a threonine ($^9$KS$^{11}$T(phosphorylated)GGKAPR) (P-11P) and the bottom line illustrates the SERS spectrum of a peptide that has been phosphorylated at a serine ($^9$K$^{10}$S(phosphorylated)TGGKAPR) (P-10P). Data represents spectra obtained from phosphorylated peptides from a single source. Spectra were taken at concentration of 90 ng/μL and arbitrarily offset along the y-axis.

While the relative ratio of peaks is altered by trimethylation at different positions as shown in FIG. 14A, phosphorylation at different amino acid positions is marked by spectral signature changes. FIG. 14B illustrates the spectral differences between peptides phosphorylated at serine-10 (peptide P-1 OP, $^9$K$^{10}$S$_{PO3}$TGGKAPR) and threonine-11 (peptide 11-P, $^9$KS$^{11}$T$_{PO3}$GGKAPR). A strong peak at 628 $cm^{-1}$ is present in the case of the peptide P-11P and not in the peptide P-10P. It should be noted that these results were obtained from phosphorylated peptides obtained from a single supplier source. In the case of phosphorylation modification, the spectral differences are likely due to the negatively charged phosphate groups affecting the adsorption and orientation of the peptides onto the silver nanoparticles.

While only certain features of the invention have been illustrated and described herein, many modifications and changes will occur to those skilled in the art. It is, therefore, to be understood that the appended claims are intended to cover all such modifications and changes as fall within the true spirit of the invention.

The improved SERS and SECARS device of the embodiments of this invention could also be used for therapeutic materials development, i.e., for drug development and for biomaterial studies, as well as for biomedical research, analytical chemistry, high throughput compound screening, and bioprocess monitoring. Yet other applications of the device of the embodiments of the invention could be for developing new materials, particularly nanomaterials for many purposes including, but not limited to corrosion resistance, battery energy storage, electroplating, low voltage phosphorescence, bone graft compatibility, resisting fouling by marine organisms, superconductivity, epitaxial lattice matching, or chemical catalysis.

The embodiments of this invention have yet other several practical uses. For example, one embodiment of the invention allows molecules and nanomaterials detection/analysis based on the electrical readout of specific captured Raman signals (fingerprints) of molecules and nanomaterials. Another embodiment of the invention has potential applications for nanomaterials study to be used in electronic devices (transistors and interconnects) as well as well as for detection of bio-species (DNA, protein, viruses etc.) for molecular diagnostics, homeland security, drug discovery and life science R&D work.

This application discloses several numerical range limitations that support any range within the disclosed numerical ranges even though a precise range limitation is not stated verbatim in the specification because the embodiments of the invention could be practiced throughout the disclosed numerical ranges. Finally, the entire disclosure of the patents and publications referred in this application, if any, are hereby incorporated herein in entirety by reference.

The invention claimed is:

1. A device comprising at least one laser, a sample stage and a detector,
   wherein the sample stage is moveable in a plurality of directions and comprises a SERS active material,
   wherein the device comprises at least two lasers.

2. The device of claim 1, further comprising a non-dispersive spectrograph.

3. The device of claim 1, further comprising a dispersive spectrograph.

4. The device of claim 1, wherein the device is adapted to produce at least two laser beams of different wavelengths.

5. The device of claim 4, further comprising a dichroic mirror that is adapted to produce spatial overlap of said at least two laser beams and an autocorrelator adapted to monitor temporal overlap of said at least two laser beams.

6. The device of claim 1, further comprising a phase lock adapted to compare laser pulses generated by said at least two lasers.

7. The device of claim 1, further comprising a scanning mirror adapted to steer a laser beam across a surface of the sample stage.

8. The device of claim 1, further comprising an optical parametric oscillator adapted to produce at least one laser beam.

9. The device of claim 1, further comprising a laser line filter, a half-waveplate, a bandpass filter and a polarizer.

10. A device comprising at least one laser, a scanning mirror, a sample stage comprising a SERS active material and a detector, wherein the scanning mirror is adapted to steer a laser beam across a surface of the sample stage,
    wherein the device comprises at least two lasers.

11. The device of claim 10, further comprising a non-dispersive spectrograph.

12. The device of claim 10, further comprising a dispersive spectrograph.

13. The device of claim 10, wherein the device is adapted to produce at least two laser beams of different wavelengths.

14. The device of claim 13, further comprising a dichroic mirror that is adapted to produce spatial overlap of said at least two laser beams and an autocorrelator adapted to monitor temporal overlap of said at least two laser beams.

15. The device of claim 10, further comprising a phase lock adapted to compare laser pulses generated by said at least two lasers.

16. The device of claim 10, wherein the sample stage is moveable in at least Z direction.

17. The device of claim 10, further comprising an optical parametric oscillator adapted to produce at least one laser beam.

18. The device of claim 10, further comprising a laser line filter, a half-waveplate, a bandpass filter and a polarizer.

19. A method of manufacturing a device comprising placing at least one laser, placing a sample stage and placing a detector, wherein the sample stage is moveable in a plurality of directions and comprises a SERS active material,
    wherein the device comprises at least two lasers.

20. The method of claim 19, wherein the device is adapted to produce at least two laser beams of different wavelengths, further comprising placing a dichroic mirror that is adapted to produce spatial overlap of said at least two laser beams and placing an autocorrelator that is adapted to monitor temporal overlap of said at least two laser beams.

21. The method of claim 19, wherein the device comprises at least two lasers, further comprising placing a phase lock that is adapted to compare laser pulses generated by said at least two lasers.

22. The method of claim 19, further comprising placing a dispersive spectrograph.

23. The method of claim 19, further comprising placing a non-dispersive spectrograph.

24. The method of claim 19, further comprising placing a scanning mirror that is adapted to steer a laser beam across a surface of the sample stage.

25. The method of claim 19, further comprising placing an optical parametric oscillator that is adapted to produce at least one laser beam.

26. A method of manufacturing a device comprising placing at least one laser, placing a scanning mirror, placing a sample stage comprising a SERS active material and placing a detector, wherein the scanning mirror is adapted to steer a laser beam across a surface of the sample stage,
    wherein the device comprises at least two lasers.

27. The method of claim 26, wherein the device is adapted to produce at least two laser beams of different wavelengths, further comprising placing a dichroic mirror that is adapted to produce spatial overlap of said at least two laser beams and placing an autocorrelator that is adapted to monitor temporal overlap of said at least two laser beams.

28. The method of claim 26, wherein the device comprises at least two lasers, further comprising placing a phase lock that is adapted to compare laser pulses generated by said at least two lasers.

29. The method of claim 26, further comprising placing a dispersive spectrograph.

30. The method of claim 26, further comprising placing a non-dispersive spectrograph.

31. The method of claim 26, further comprising placing a scanning mirror that is adapted to steer a laser beam across a surface of the sample stage.

32. The method of claim 26, further comprising placing an optical parametric oscillator that is adapted to produce at least one laser beam.

33. A method of imaging comprising a SECARS equipment, the method comprising forming at least two laser beams of different wavelengths, creating a spatial overlap of said at least two laser beams, and creating a temporal overlap of said at least two laser beams, directing said at least two laser beams on a surface of a sample stage that is moveable in a plurality of directions and comprises a SERS active material.

34. The method of claim 33, further comprising monitoring a wavelength of said at least two laser beams, tuning said at least two laser beams, monitoring a pulse width of said at least two laser beams and engaging a phase lock so that a phase delay between said at least two laser beams is contact.

35. The method of claim 34, further moving a sample placed on the sample stage or steering said at least two laser beams across the sample.

36. The method of claim 35, further comprising collecting a SECARS signal.

37. The method of claim 36, further comprising processing the SECARS signal to identify the sample.

* * * * *